United States Patent
Cook et al.

(10) Patent No.: US 11,149,315 B2
(45) Date of Patent: Oct. 19, 2021

(54) METHOD FOR PREDICTING CERVICAL SHORTENING AND PRETERM BIRTH

(71) Applicant: IMPERIAL COLLEGE OF SCIENCE, TECHNOLOGY, AND MEDICINE, London (GB)

(72) Inventors: Joanna Cook, London (GB); Philip Bennett, London (GB); Vasiliki Terzidou, London (GB); David Macintyre, London (GB)

(73) Assignee: IMPERIAL COLLEGE OF SCIENCE, TECHNOLOGY, AND MEDICINE, London (GB)

(*) Notice: Subject to any disclaimer, the term of this patent is extended or adjusted under 35 U.S.C. 154(b) by 0 days.

(21) Appl. No.: 16/880,766

(22) Filed: May 21, 2020

(65) Prior Publication Data

US 2020/0362411 A1 Nov. 19, 2020

Related U.S. Application Data

(63) Continuation of application No. 15/555,900, filed as application No. PCT/GB2016/050618 on Mar. 7, 2016, now Pat. No. 10,689,704.

(30) Foreign Application Priority Data

Mar. 6, 2015 (GB) .................................. 1503792.2

(51) Int. Cl.
 *C12Q 1/6883* (2018.01)
 *C12Q 1/6869* (2018.01)

(52) U.S. Cl.
 CPC ......... *C12Q 1/6883* (2013.01); *C12Q 1/6869* (2013.01); *C12Q 2600/112* (2013.01);
 (Continued)

(58) Field of Classification Search
 CPC ................ C12Q 1/6869; C12Q 1/6883; C12Q 2600/112; C12Q 2600/118; C12Q 2600/158; C12Q 2600/178
 See application file for complete search history.

(56) References Cited

U.S. PATENT DOCUMENTS

| 10,689,704 B2* | 6/2020 | Cook .................. C12Q 1/6883 |
| 2012/0107825 A1 | 5/2012 | Winger et al. |
| 2013/0296190 A1 | 11/2013 | Dong et al. |

FOREIGN PATENT DOCUMENTS

| WO | 1999047706 A1 | 9/1999 |
| WO | 1999058974 | 11/1999 |
| | (Continued) | |

OTHER PUBLICATIONS

Pessi, T. et al. SpringerPlus 4:206 (Apr. 2015). (Year: 2015).*
(Continued)

*Primary Examiner* — Diana B Johannsen
(74) *Attorney, Agent, or Firm* — Morgan, Lewis & Bockius LLP

(57) ABSTRACT

The present invention provides method for predicting risk of cervical shortening, methods for predicting risk of preterm labour (PTL), and methods for characterising a pregnant subject having a history of previous PTL, mid-trimester loss or cervical cone biopsy as being in need of surveillance and/or intervention to prevent preterm labour, comprising determining the expression level of one or more of the miRNA molecules identified in Table 1 or Table 2 extracted from a biological sample obtained from said subject and comparing to a control value. Biochips and kits for use in carrying out the methods of the invention are also provided.

15 Claims, 19 Drawing Sheets

Specification includes a Sequence Listing.

(52) U.S. Cl.
CPC .. *C12Q 2600/118* (2013.01); *C12Q 2600/158* (2013.01); *C12Q 2600/178* (2013.01)

(56) References Cited

FOREIGN PATENT DOCUMENTS

| WO | 2009093254 A2 | 7/2009 |
|---|---|---|
| WO | 2011098783 | 8/2011 |
| WO | 2012/08369 A2 | 6/2012 |
| WO | 2012075150 A2 | 6/2012 |

OTHER PUBLICATIONS

Fu, Guodong et al: 11 MicroRNAs in Human Placental Development and Pregnancy Complications, International Journal of Molecular Sciences, vol. 14, No. 3, Mar. 8, 2013 (Mar. 8, 2013), pp. 5519-5544.

Zhu X M et al: 11 Differential expression profile of microRNAs in human placentas from preeclamptic pregnancies vs normal pregnancies 11, American Journal of Obstetrics & Gynecology, vol. 200, No. 6, Jun. 1, 2009 (Jun. 1, 2009), pp. 661.e1-661.e7.

Chan H-W et al. "The expression of the let-7 miRNAs and Lin28 signalling pathway in human term gestational tissues" Placenta 34:443-448, 2013.

Elovitz Michal A et al. "Distinct cervical microRNA profiles are present in women destined to have a preterm birth" Am J Obstet Gynecol 221.e2-221.e11, Mar. 2014.

Elovitz Michal A et al. "Can microRNA profiling in maternal blood identify women at risk for preterm birth?" Am J Obstet Gynecol 212:782.e1-5, Jun. 2015.

Yogev Yariv et al. "Spontaneous Preterm Labor—A Possible Role for Micro-RNA" Am J Obstet Gynecol S44:110, Dec. 2007 (abstract).

International Patent Application No. PCT/GB2016/050618 International Search Report and Written Opinion dated Jul. 26, 2016, 17 pages.

International Patent Application No. PCT/GB2016/050618 International Preliminary Report on Patentability dated Sep. 12, 2017, 11 pages.

Wood, N. S., Marlow, N., Costeloe, K., Gibson, A. T. & Wilkinson, A. R. Neurologic and developmental disability after extremely preterm birth. EPICure Study Group. The New England Journal of Medicine 343, 378-384 (2000).

Holst, R. M., et al. Prediction of spontaneous preterm delivery in women with preterm labor: analysis of multiple proteins in amniotic and cervical fluids. Obstetrics and Gynecology 114, 268-277 (2009).

Mitchell, P. S., et al. Circulating microRNAs as stable blood-based markers for cancer detection. Proceedings of the National Academy of Sciences of the United States of America 105, 10513-10518 (2008).

Harper, K. A. & Tyson-Capper, A. J. Complexity of COX-2 gene regulation. Biochemical Society transactions 36, 543-545 (2008).

Luense, L.J., Carletti, M. Z. & Christenson, L. K. Role of Dicer in female fertility. Trends in endocrinology and metabolism: TEM 20, 265-272 (2009).

Morita, S., et al. One Argonaute family member, Eif2c2 (Ago2), is essential for development and appears not to be involved in DNA methylation. Genomics 89, 687-696 (2007).

Mouillet, J. F., et al. The levels of hypoxia-regulated microRNAs in plasma of pregnant women with fetal growth restriction. Placenta 31, 781-784 (2010).

Renthal. N. E .. et al. miR-200 family and targets. ZEB1 and ZEB2, modulate uterine quiescence and contractility during pregnancy and labor. Proceedings of the National Academy of Sciences of the United States of America 107, 20828-20833 (2010).

Williams, K. C., Renthal, N. E., Condon, J. C., Gerard, R. D. & Mendelson, C. R. MicroRNA-200a serves a key role in the decline of progesterone receptor function leading to term and preterm labor. Proceedings of the National Academy of Sciences of the United States of America 109, 7529-7534 (2012).

Hassan, S. S., et al. MicroRNA expression profiling of the human uterine cervix after term labor and delivery. American journal of obstetrics and gynecology 202, 80 e81-88 (2010).

Geiss, G. K., et al. Direct multiplexed measurement of gene expression with color-coded probe pairs. Nature biotechnology 26, 317-325 (2008).

Campbell, S. Universal cervical-length screening and vaginal progesterone prevents early preterm births, reduces neonatal morbidity and is cost saving: doing nothing is no longer an option. Ultrasound in obstetrics & gynecology: the official journal of the International Society of Ultrasound in Obstetrics and Gynecology 38, 1-9 (2011).

Romero, R., et al. A blueprint for the prevention of preterm birth: vaginal progesterone in women with a short cervix. Journal of perinatal medicine 41, 27-44 (2013).

Montenegro, D., et al. Differential expression of microRNAs with progression of gestation and inflammation in the human chorioamniotic membranes. Am. J. Obstet. Gynecol. Sep. 2007; 197(3): 289.e1-289.e6.

Nold, C. et al, "Prevention of preterm birth by progestational agents: what are the molecular mechanisms?," Am. J. Obstet. Gynecol., vol. 208, 2013: 223, e 1-7.

Qiagen catalogue, 2010, "RT 2 Profile PCR Array Human let-7 Targets", Product No. 330231, catalogue No. PAHS-6008Z available online at: http://www.sabiosciences.com/rt_per_producUHTML/PAHS-6008Z.html.

Zhao, Z. et al. Clinical Biochemistry 46:953 (2013).

Morales-Prieto, D. et al. Journal of Reproductive Immunology 97:51 (2013).

Jang, J. et al. BMC Genomics 12:144 (2011).

miRBase, Accession No. MIMAT0000451, 2 pages (downloaded Mar. 31, 2019).

Mrjmand, M. "MIR150", Atlast of Genetics and Cytogenetics, 11 pages (downloaded Apr. 1, 2019).

Oleson, A. et al. BMJ 326:476 (Mar. 2003).

Punga, T. et al. Annals of Clinical and Translational Neurology 1 (1):49 (2014).

Hoff, J. et al. Neurology 61: 1362 (2003).

Examination Report dated Jul. 24, 2019 for European Patent Application No. 16709550.4, 12 pages.

Examination Report dated Jan. 27, 2020 for European Patent Application No. 16709550.4, 7 pages.

W. Wang et al., MicroRNA profiling of follicular lymphoma identifies micro RNAs related to cell proliferation and tumor response, Haematologica, vol. 97, No. 4, Apr. 1, 2012 (Apr. 1, 2012), pp. 586-594.

Extended European Search Report dated May 27, 2020 for European Patent Application No. 20213489.6, 12 pages.

\* cited by examiner

SEQUENCE LISTING

<160> NUMBER OF SEQ ID NOS: 24

<210> SEQ ID NO 1
<211> LENGTH: 22
<212> TYPE: RNA

<213> ORGANISM: Homo sapiens

<400> SEQUENCE: 1
ugagguagua gguuguauag uu                                      22

<210> SEQ ID NO 2
<211> LENGTH: 22
<212> TYPE: RNA
<213> ORGANISM: Homo sapiens

<400> SEQUENCE: 2
uuauaauaca accugauaag ug                                      22

<210> SEQ ID NO 3
<211> LENGTH: 22
<212> TYPE: RNA
<213> ORGANISM: Homo sapiens

<400> SEQUENCE: 3
uagcagcaca ucaugguuua ca                                      22

<210> SEQ ID NO 4
<211> LENGTH: 23
<212> TYPE: RNA
<213> ORGANISM: Homo sapiens

<400> SEQUENCE: 4
ugugcaaauc caugcaaaac uga                                     23

<210> SEQ ID NO 5
<211> LENGTH: 21
<212> TYPE: RNA
<213> ORGANISM: Homo sapiens

<400> SEQUENCE: 5
aucacauugc cagggauuuc c                                       21

<210> SEQ ID NO 6
<211> LENGTH: 23
<212> TYPE: RNA
<213> ORGANISM: Homo sapiens

<400> SEQUENCE: 6
caaagugcug uucgugcagg uag                                     23

<210> SEQ ID NO 7
<211> LENGTH: 22
<212> TYPE: RNA
<213> ORGANISM: Homo sapiens

<400> SEQUENCE: 7
ucucccaacc cuuguaccag ug                                      22

<210> SEQ ID NO 8
<211> LENGTH: 22
<212> TYPE: RNA
<213> ORGANISM: Homo sapiens

<400> SEQUENCE: 8
uggagagaaa ggcaguuccu ga                                      22

<210> SEQ ID NO 9
<211> LENGTH: 23

```
<212> TYPE: RNA
<213> ORGANISM: Homo sapiens

<400> SEQUENCE: 9
caacggaauc ccaaaagcag cug                                            23

<210> SEQ ID NO 10
<211> LENGTH: 21
<212> TYPE: RNA
<213> ORGANISM: Homo sapiens

<400> SEQUENCE: 10
uaaagugcug acagugcaga u                                              21

<210> SEQ ID NO 11
<211> LENGTH: 22
<212> TYPE: RNA
<213> ORGANISM: Homo sapiens

<400> SEQUENCE: 11
aagcugccag uugaagaacu gu                                             22

<210> SEQ ID NO 12
<211> LENGTH: 21
<212> TYPE: RNA
<213> ORGANISM: Homo sapiens

<400> SEQUENCE: 12
uucaaguaau ucaggauagg u                                              21

<210> SEQ ID NO 13
<211> LENGTH: 22
<212> TYPE: RNA
<213> ORGANISM: Homo sapiens

<400> SEQUENCE: 13
ugagguagua guuugugcug uu                                             22

<210> SEQ ID NO 14
<211> LENGTH: 20
<212> TYPE: RNA
<213> ORGANISM: Homo sapiens

<400> SEQUENCE: 14
ggauccgagu cacggcacca                                                20

<210> SEQ ID NO 15
<211> LENGTH: 20
<212> TYPE: RNA
<213> ORGANISM: Homo sapiens

<400> SEQUENCE: 15
uacaguauag augauguacu                                                20

<210> SEQ ID NO 16
<211> LENGTH: 22
<212> TYPE: RNA
<213> ORGANISM: Homo sapiens

<400> SEQUENCE: 16
ugucaguuug ucaaauaccc ca                                             22

<210> SEQ ID NO 17
```

```
<211> LENGTH: 22
<212> TYPE: RNA
<213> ORGANISM: Homo sapiens

<400> SEQUENCE: 17
uauugcacuu gucccggccu gu                                              22

<210> SEQ ID NO 18
<211> LENGTH: 22
<212> TYPE: RNA
<213> ORGANISM: Homo sapiens

<400> SEQUENCE: 18
ugagguagua gguugugugg uu                                              22

<210> SEQ ID NO 19
<211> LENGTH: 21
<212> TYPE: RNA
<213> ORGANISM: Homo sapiens

<400> SEQUENCE: 19
caucccuugc augguggagg g                                               21

<210> SEQ ID NO 20
<211> LENGTH: 22
<212> TYPE: RNA
<213> ORGANISM: Homo sapiens

<400> SEQUENCE: 20
uagcagcacg uaaauauugg cg                                              22

<210> SEQ ID NO 21
<211> LENGTH: 22
<212> TYPE: RNA
<213> ORGANISM: Homo sapiens

<400> SEQUENCE: 21
ugagguagua guuuguacag uu                                              22

<210> SEQ ID NO 22
<211> LENGTH: 22
<212> TYPE: RNA
<213> ORGANISM: Homo sapiens

<400> SEQUENCE: 22
ucagugcauc acagaacuuu gu                                              22

<210> SEQ ID NO 23
<211> LENGTH: 22
<212> TYPE: RNA
<213> ORGANISM: Homo sapiens
```

-continued

```
<400> SEQUENCE: 23
uggaguguga caaugguguu ug                                          22

<210> SEQ ID NO 24
<211> LENGTH: 23
<212> TYPE: RNA
<213> ORGANISM: Artificial
<220> FEATURE:
<223> OTHER INFORMATION: Synthetic normalisation sequence

<400> SEQUENCE: 24
ugcaaaucuu ucgcgacugu agg                                         23
```

METHOD FOR PREDICTING CERVICAL SHORTENING AND PRETERM BIRTH

CROSS-REFERENCE TO RELATED APPLICATIONS

This application is a continuation of U.S. patent application Ser. No. 15/555,900 filed Sep. 5, 2017, which is a 35 U.S.C. § 371 national phase application of International Patent Application No. PCT/GB2016/050618, filed on Mar. 7, 2016, which claims priority to GB Application No. 1503792.2, filed Mar. 6, 2015. These applications are incorporated by reference herein in their entireties.

FIELD OF THE INVENTION

The present invention relates to microRNAs (miRNAs) that are useful in predicting cervical shortening and preterm birth. The invention provides methods and kits for predicting risk of cervical shortening, preterm labour and for identifying pregnant subjects in need of interventions to prevent preterm labour.

BACKGROUND OF THE INVENTION

Of 600,000 UK live births per annum, approximately 8,000 will be at birth weights below 1500 g, which equates to a gestational age of less than 32 weeks. Of these preterm babies, 1600 will die and a further 600 will develop cerebral palsy. The impact of disability increases dramatically when delivery occurs close to the limits of viability at around 24 weeks. The EPICURE study described how 25% of babies born before 25 weeks who survive to be discharged from hospital develop severe disability, 25% mild disability and less than 50% are developmentally normal at 30 months of age[1]. The economic impact of providing long-term health and social care for these families is therefore significant.

Preterm labour (PTL) is a syndrome, not a single disease process. Some aetiologies, for example placental abruption, are unpredictable and unpreventable. Maternal and/or fetal 'stress' may cause preterm labour by cortisol-mediated effects upon placental CRH. Multiple pregnancy causes preterm delivery both through placental CRH and through mechanical stretch of the uterus and cervix. But these are, in general, causes of 'late' preterm labour with less severe medical and economic sequelae.

In normal pregnancy, the onset of contractions is preceded by several weeks of cervical change characterised by decreased collagen and increased water content, identifiable clinically as effacement and shortening or cervical 'ripening'. Cervical ripening is mediated by prostaglandin and cytokine secretion in the lower pole of the uterus and associated with an inflammatory cell infiltration. The later onset of uterine contractions is mediated by up regulation of a group of 'contraction-associated proteins' (CAPs) such as prostaglandin and oxytocin receptors, and gap junctions whose expression is repressed by progesterone. Preterm delivery prior to 32 weeks is associated with chorioamnionitis and ascending bacterial infection but recent studies have shown that most cases of early preterm labour cannot be attributed solely to ascending infection.

Classical cervical incompetence (secondary to a congenital weakness or acquired following destructive cervical surgery) is a cause of second trimester pregnancy loss and early preterm delivery, and it is now accepted that cervical competence is a continuum. In women whose cervix is short or weak, the biochemical processes of cervical ripening may occur because of stretch in the lower pole of the uterus. This leads to further softening and shortening of the cervix and so to a vicious cycle. Bacteria may then gain access to the uterus and therefore the final preterm delivery appears to be associated with infection although the initial initiating factors were not infection specific. There is a poor correlation between the inflammatory response, which stimulates preterm labour, and the number of bacteria present. In some women there is an exaggerated inflammatory response to trivial numbers of bacteria. This leads similarly to ripening and shortening of the cervix allowing further bacteria to gain access to the uterus and ultimately to a form of preterm delivery clinically indistinguishable to that associated with a weakened cervix. It is therefore possible that, if women at risk of early preterm labour can be identified, an intervention which effectively switches off the biochemical processes leading to cervical shortening may prevent or delay the onset of preterm labour and therefore significantly improve neonatal outcome.

Current approaches for the prediction of PTL are limited. PTL can be predicted in those known to be at increased risk by serial measurement of cervical length (CL) on transvaginal ultrasound. Women who have had a previous PTL, mid-trimester loss (MTL) or cervical cone biopsy are eligible for CL screening, though provision in the UK is not universal.

Women with cervical shortening are at increased risk of spontaneous preterm delivery, but remain asymptomatic until preterm labour is imminent. Early interventions to prolong pregnancy are available, but can only be delivered if obstetricians are aware that cervical shortening has occurred. Vaginal ultrasound can be used to diagnose cervical shortening, but is expensive and invasive, and therefore only available to a limited number of women attending specialist centres.

If the CL is found to be less than 25 mm there are two available interventions: cervical cerclage and progesterone treatment. Cerclage acts not only to support a weak cervix, but to retain the anti-bacterial mucous plug and prevent stretch mediated activation of inflammation. Progesterone treatment is effective and probably acts via inhibition of contraction associated proteins and nuclear factor kB expression.

However, CL surveillance clinics are labour intensive, expensive and do not provide care and intervention for women without pre-existing risk factors. In addition, using only past medical history to screen for eligibility lacks sensitivity and >80% of women attending such a service do not require any intervention and deliver at term gestations.

It has been suggested that routine measurement of cervical length at 18 to 22 weeks, linked to progesterone therapy, should be offered to the entire obstetric population[12][13]. However, this would be potentially costly.

A panel of biomarkers, routinely measured in all pregnancies, which are able to predict future cervical change or PTL itself would therefore be of great value in more accurately targeting pregnant women for surveillance and therapy. Only one biomarker is currently available to predict PTL; fetal fibronectin (fFN) in cervical or vaginal fluid. fFN is not useful in the distant prediction of early PTL because it is normally present in cervical secretions at up to 22 weeks gestation. Amniotic fluid or cervical secretion cytokines levels will also predict PTL but only close to the onset of labour[2]. All pregnant women currently undergo blood testing to screen for Rhesus group and viral infections at 13 weeks of pregnancy; this is an ideal time to screen for risk of early PTL and sufficiently early to allow enrolment in a surveillance program and delivery of an intervention.

Careful regulation of gene expression in the myometrium and fetal membranes is central to controlling the timing of labour onset. miRNAs are small, single-stranded, 19-25 nucleotide molecules that have emerged as important regulators of gene expression in almost all eukaryotes; a third of the protein encoding human genome is thought to be regulated by miRNAs. miRNAs are non-coding RNAs and function in a manner similar to small-interfering RNA to down-regulate gene expression at the post-transcriptional level. miRNA biogenesis involves a series of steps that lead to gene silencing. Briefly, miRNAs are transcribed in the nucleus as longer primary-miRNAs, which are cleaved to form hair-pin shaped precursor-miRNAs. These precursors are exported from the nucleus and further cleaved to form the mature miRNA which associates with the RNA induced silencing complex to target the 3'-untranslated region of specific mRNAs and inhibit their translation to protein. miRNAs are present in a cell free state in plasma and remain stable and easily measurable. Their potential utility as a biomarker of disease or response to treatment has consequently been widely acknowledged[3].

miRNAs are expressed in a tissue specific manner and therefore their differential expression, both spatially and over time, is a potentially rich area of research. miRNA expression in the chorioamniotic membranes, placenta, umbilical cord and myometrium is currently being investigated by a number of groups. Cyclo-oxygenase 2 (COX2) (which catalyses the synthesis of prostaglandin which in turn modulates uterine contractions) is regulated at the post-transcriptional level through changes in specific miRNAs[4]. In addition, knockout studies of proteins essential for miRNA biogenesis have demonstrated that miRNAs play an essential role in reproduction. DICER is an RNAse III endonuclease that is essential for the biogenesis of miRNAs and small interfering (si)RNAs, and loss of DICER within ovarian granulosa cells, luteal tissue, oocyte, oviduct and potentially the uterus, renders murine females infertile[5]. In addition, disruption of the gene for Ago 2, another important component of RNA interference (RNAi) leads to embryo death early after implantation[6]. Intriguingly, placental miR-NAs are also released into the maternal circulation. They remain stable and are easily detectable in blood and it has therefore been proposed that they might provide novel, non-invasive biomarkers for placental disorders such as preeclampsia or fetal growth restriction[7].

Current understanding of how miRNA expression may regulate human myometrial gene expression and hence contractions, is limited. Renthal et al found that the miR-200 family of miRNAs is up-regulated in the labouring murine and human myometrium at term[8]. ZEB1 and ZEB2 were identified as two targets of this group in functional studies, and were found to be co-ordinately down-regulated in mouse models of PTL. ZEB1 and ZEB2 act as transcriptional repressors, which may inhibit the expression of contraction associated genes, oxytocin receptor and connexin-43, and block oxytocin induced contractility in cultured myometrial cells.

Williams et al linked miR-200a to progesterone metabolism through the repression of STAT5b, a transcriptional repressor of the P4 metabolising enzyme 20α-hydroxysteroid dehydrogenase, in the mouse and human uterus[9]. It is unclear how this is relevant to humans where labour is not associated with a reduction in circulating progesterone.

Recently, a study examining the global expression of miRNAs in cervical tissue from women following vaginal delivery at term or pre-labour LSCS, described 226 miRNAs expressed in the cervix[10]. Furthermore, miR-223, miR-34b and miR-34c were found to have increased expression with labour. Montenegro et al. examined miRNA expression in the fetal membranes in four distinct cohorts: term NL & L, and PTL with or without histological chorioamnionitis[14]. The authors detected 153 and 152 different miRNAs in at least 50% of samples in the term and preterm groups respectively. They found no difference in the term NL and term L groups, but described 13 miRNAs with reduced expression with advancing gestational age. They also found miR-223 and miR-338 had increased in expression in PTL membranes in the presence of inflammation.

SUMMARY OF THE INVENTION

According to a first aspect, the present invention provides a method for predicting risk of cervical shortening in a pregnant female subject, comprising determining the expression level of one or more of the miRNA molecules identified in Table 1 or Table 2 extracted from a biological sample obtained from said subject and comparing to a control value, wherein a difference in the expression level of the one or more of the miRNA molecules compared to the control value indicates that the subject is at high or low risk of cervical shortening.

According to a second aspect, the invention provides a method for predicting risk of preterm labour (PTL) in a pregnant female subject, comprising determining the expression level of one or more miRNA molecules identified in Table 1 or Table 2 extracted from a biological sample obtained from said subject and comparing to a control value, wherein a difference in the expression level of the one or more of the miRNA molecules compared to the control value indicates that the subject is at high or low risk of PTL.

According to a third aspect, the invention provides a method for characterising a pregnant female subject having a history of previous PTL, mid-trimester loss or cervical cone biopsy as being in need of cervical ultrasound screening, cervical cerclage and/or progesterone therapy, comprising determining the expression level of one or more miRNA molecules identified in Table 1 or Table 2 extracted from a biological sample obtained from said subject and comparing to a control value, wherein a difference in the expression level of the one or more of the miRNA molecules compared to the control value indicates that the subject is in need of cervical ultrasound screening, cervical cerclage and/or progesterone therapy.

According to a fourth aspect, the invention provides a method for predicting the timing of the onset of labour in a pregnant subject who is at term (>37 weeks gestation), comprising determining the expression level of one or more miRNA molecules identified in Table 1 or Table 2 extracted from a biological sample obtained from said subject and comparing to a control value, wherein a difference in the expression level of the one or more of the miRNA molecules compared to the control value indicates the timing of the onset of labour.

According to a fifth aspect, the invention provides a solid substrate comprising one or more probes specific for one or more of the miRNA molecules in Table 1 or Table 2.

A sixth aspect of the invention is directed to the use of a solid substrate according to the fourth aspect of the invention in a method according to any of the first, second or third aspects of the invention.

A seventh aspect of the invention provides a kit for predicting risk of cervical shortening in a pregnant female subject, comprising one or more probes specific for one or more of the miRNA molecules in Table 1 or Table 2.

An eighth aspect of the invention provides a kit for predicting risk of preterm labour (PTL) in a pregnant female subject, comprising one or more probes specific for one or more of the miRNA molecules in Table 1 or Table 2.

DETAILED DESCRIPTION OF THE INVENTION

Figure 1:
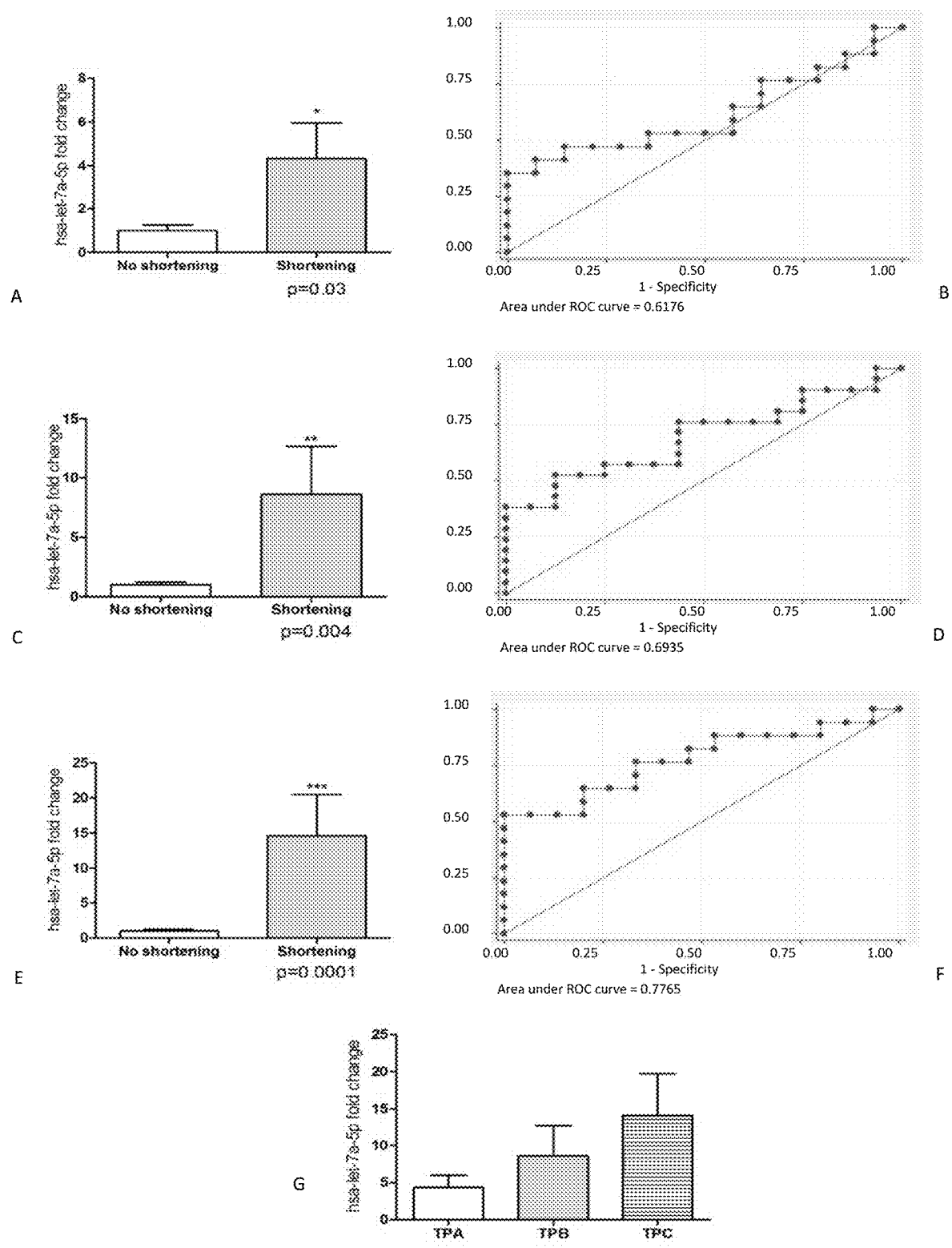
FIG. 1 relates to hsa-let-7a-5p as a predictor of cervical shortening. Expression of hsa-let-7a-5p in plasma of women whose cervix shortened to <25 mm (n=18) compared with those who did not exhibit cervical shortening (n=15), measured via real time polymerase chain reaction (RT PCR) at time point A (12-14$^{+6}$ weeks gestation) (TPA) (A). Receiver operated characteristic (ROC) curve showing sensitivity and specificity of hsa-let-7a-5p to predict cervical shortening at TPA (B) following PCR analysis (AUC=0.62). Expression of hsa-let-7a-5p in plasma of women whose cervix shortened to <25 mm (n=21) compared with those who did not exhibit cervical shortening (n=16), measured using RT PCR at time point B (15-17$^{+6}$ weeks gestation) (TPB) (C). ROC curve showing sensitivity and specificity of hsa-let-7a-5p to predict cervical shortening at TPB (AUC=0.69) (D). Expression of hsa-let-7a-5p in plasma of women whose cervix shortened to <25 mm (n=17) compared with those who did not exhibit cervical shortening (n=15), measured using RT PCR (E) at time point C (19-21$^{+6}$ weeks gestation) (TPC). ROC curve showing sensitivity and specificity of hsa-let-7a-5p to predict cervical shortening at TPC (AUC=0.78) (F). Fold change at each time point of hsa-let-7a-5p expression in plasma of women who exhibited cervical shortening compared with expression in women who had normal cervical lengths (G) Fold change increases with gestation.
Figure 2:
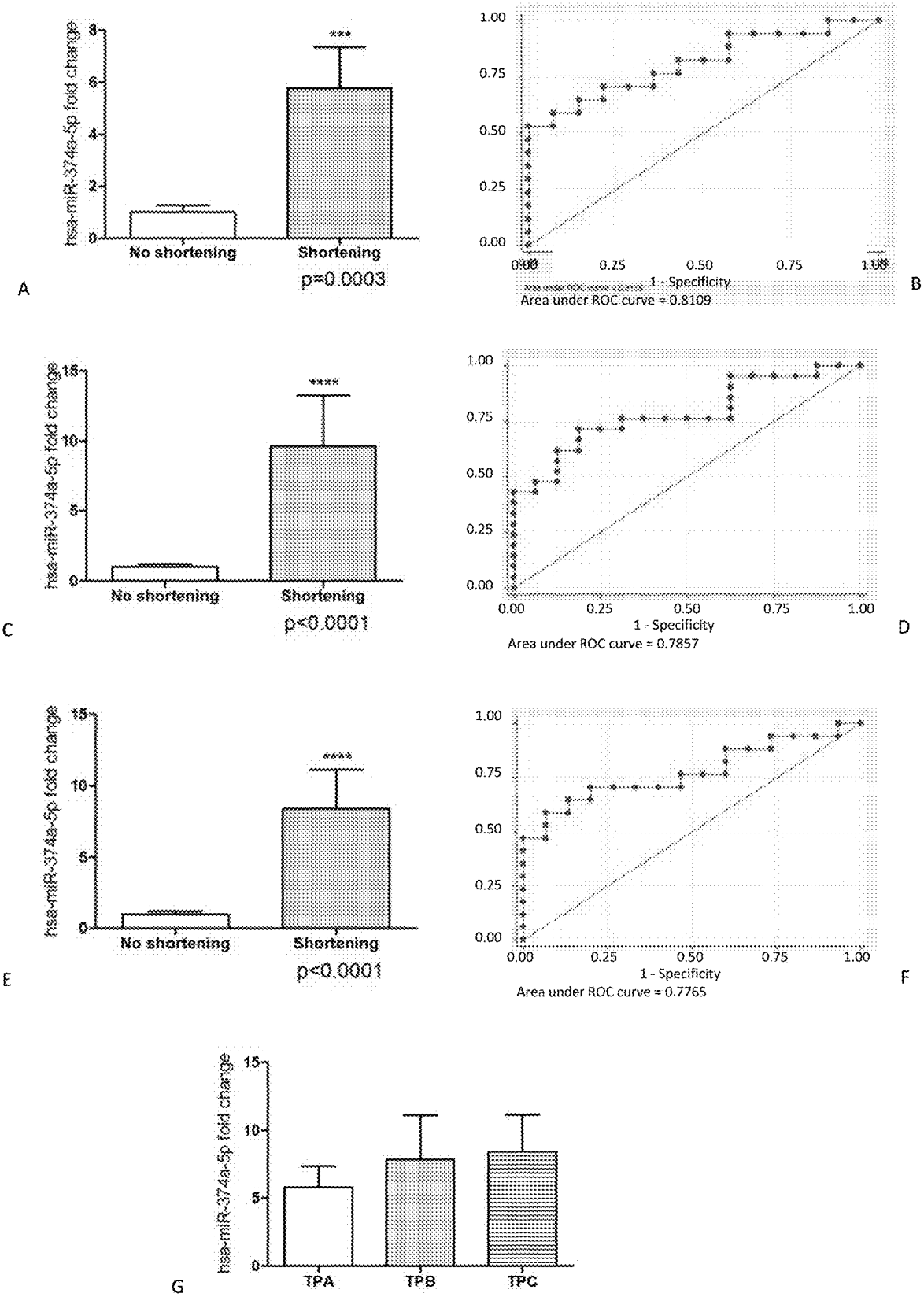
FIG. 2 relates to hsa-miR-374a-5p as a predictor of cervical shortening. Expression of hsa-miR-374a-5p in plasma of women whose cervix shortened to <25 mm (n=18) compared with those who did not exhibit cervical shortening (n=15), measured via real time polymerase chain reaction (RT PCR) at time point A (12-14$^{+6}$ weeks gestation) (TPA) (A). Receiver operated characteristic (ROC) curve showing sensitivity and specificity of hsa-miR-374a-5p to predict cervical shortening at TPA (B) following PCR analysis (AUC=0.81). Expression of hsa-miR-374a-5p in plasma of women whose cervix shortened to <25 mm (n=21) compared with those who did not exhibit cervical shortening (n=16), measured using RT PCR at time point B (15-17$^{+6}$ weeks gestation) (TPB) (C). ROC curve showing sensitivity and specificity of hsa-miR-374a-5p to predict cervical shortening at TPB (AUC=0.79) (D). Expression of hsa-miR-374a-5p in plasma of women whose cervix shortened to <25 mm (n=17) compared with those who did not exhibit cervical shortening (n=15), measured using RT PCR at time point C (19-21$^{+6}$ weeks gestation) (TPC) (E). ROC curve showing sensitivity and specificity of hsa-miR-374a-5p to predict cervical shortening at TPC (AUC=0.78) (F). Fold change of hsa-miR-374a-5p expression at each time point in plasma of women who exhibited cervical shortening, compared with expression in women who had a normal cervical length (G).
Figure 3:
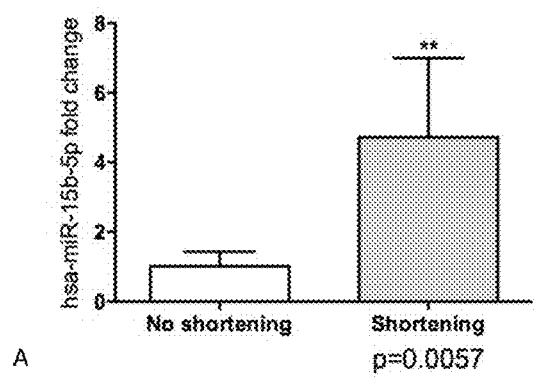
FIG. 3 relates to hsa-miR-15b-5p as a predictor of cervical shortening. Expression of hsa-miR-15b-5p in plasma of women whose cervix shortened to <25 mm (n=18) compared with those who did not exhibit cervical shortening (n=15), measured via real time polymerase chain reaction (RT PCR) at time point A (12-14$^{+6}$ weeks gestation) (TPA) (A). Receiver operated characteristic (ROC) curve showing sensitivity and specificity of hsa-miR-15b-5p to predict cervical shortening at TPA (B) following PCR analysis (AUC=0.81). Expression of hsa-miR-15b-5p in plasma of women whose cervix shortened to <25 mm (n=21) compared with those who did not exhibit cervical shortening (n=16), measured using RT PCR at time point B (15-17$^{+6}$ weeks gestation) (TPB) (C). ROC curve showing sensitivity and specificity of hsa-miR-15b-5p to predict cervical shortening at TPB (AUC=0.79) (D). Expression of hsa-miR-15b-5p in plasma of women whose cervix shortened to <25 mm (n=17) compared with those who did not exhibit cervical shortening (n=15), measured using RT PCR (E) at time point C (19-21$^{+6}$ weeks gestation) (TPC). ROC curve showing sensitivity and specificity of hsa-miR-15b-5p to predict cervical shortening at TPC (AUC=0.78) (F). Fold change of hsa-miR-15b-5p expression at each time point, in plasma of women who exhibited cervical shortening, compared with expression in women who had normal cervical lengths (G). Relative expression of hsa-miR-15b-5p increases with advancing gestation.
Figure 3:
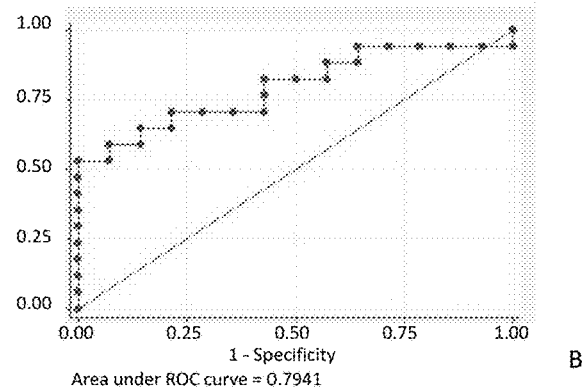
Figure 3:
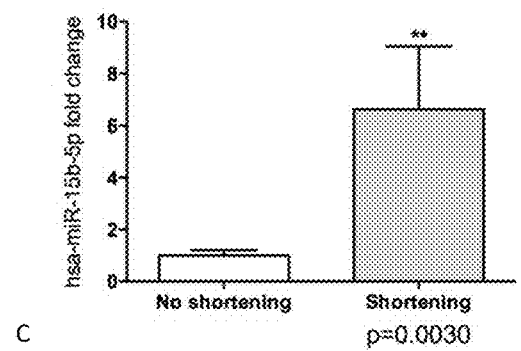
Figure 3:
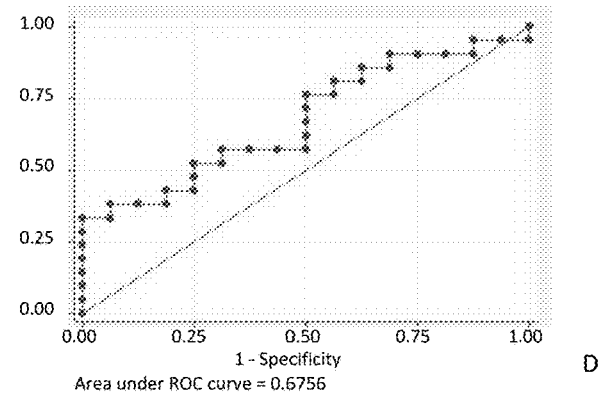
Figure 3:
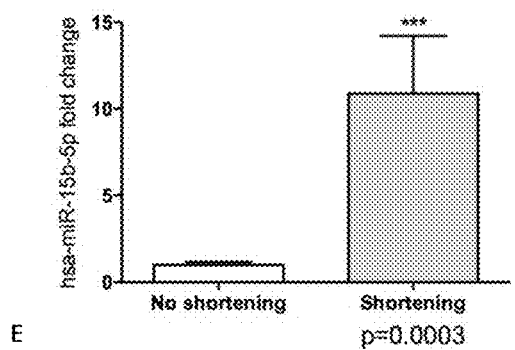
Figure 3:
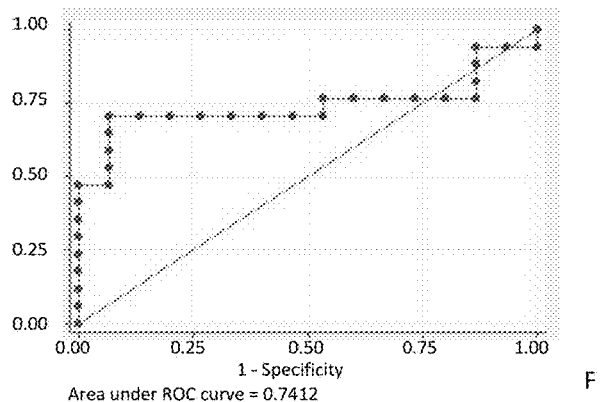
Figure 3:
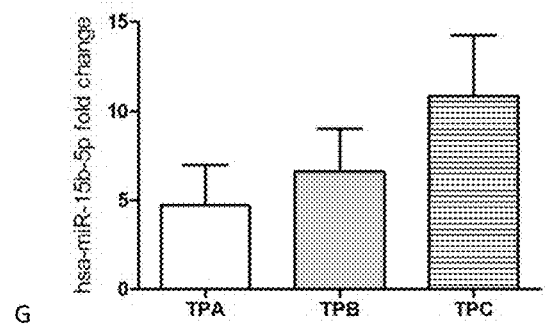
Figure 4:
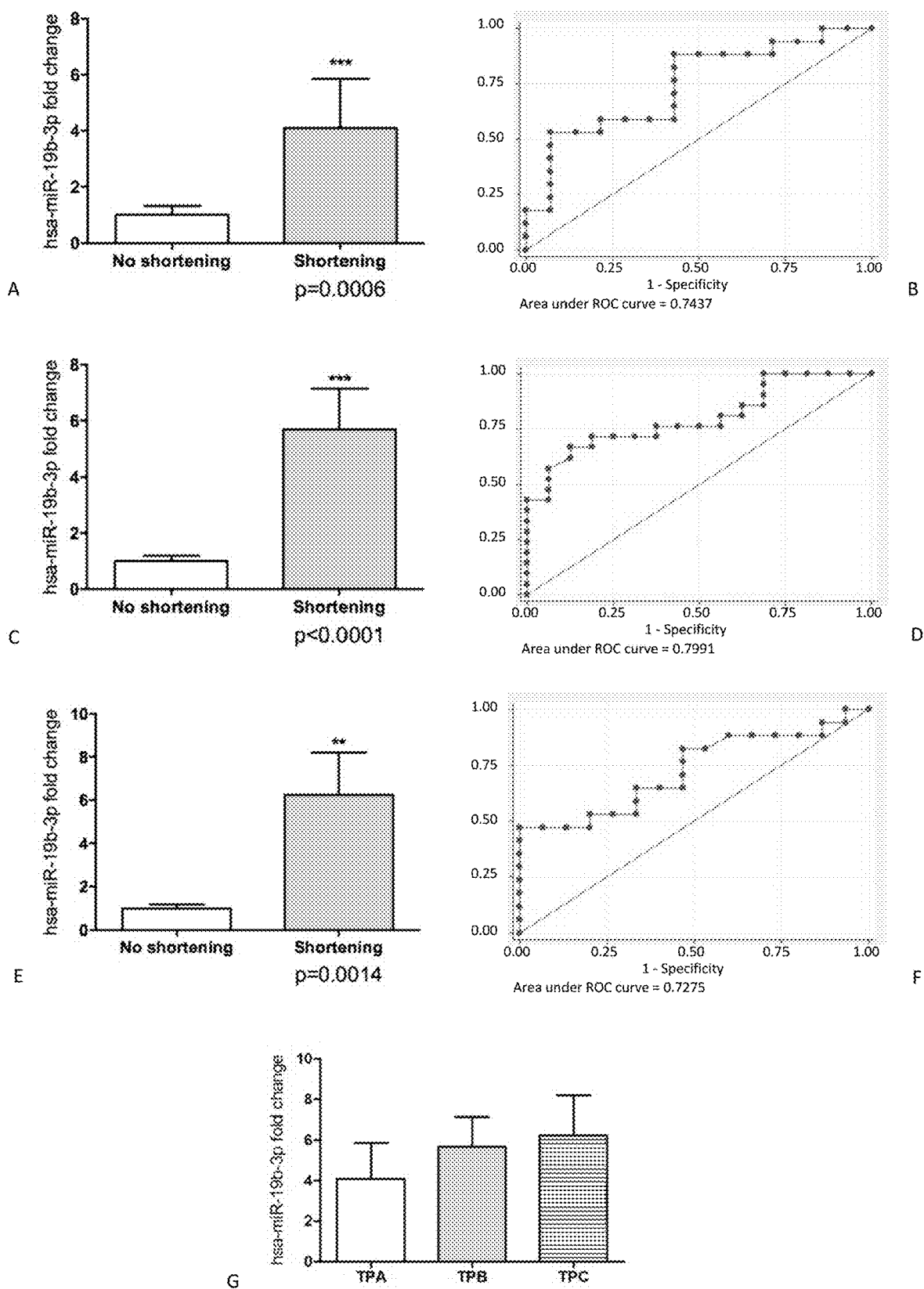
FIG. 4 relates to hsa-miR-19b-3p as a predictor of cervical shortening. Expression of hsa-miR-19b-3p in plasma of women whose cervix shortened to <25 mm (n=18) compared with those who did not exhibit cervical shortening (n=15), measured via real time polymerase chain reaction (RT PCR) at time point A (12-14$^{+6}$ weeks gestation) (TPA) (A). Receiver operated characteristic (ROC) curve showing sensitivity and specificity of hsa-miR-19b-3p to predict cervical shortening at TPA (B) following PCR analysis (AUC=0.74). Expression of hsa-miR-19b-3p in plasma of women whose cervix shortened to <25 mm (n=21) compared with those who did not exhibit cervical shortening (n=16), measured using RT PCR at time point B (15-17$^{+6}$ weeks gestation) (TPB) (C). ROC curve showing sensitivity and specificity of hsa-miR-19b-3p to predict cervical shortening at TPB (AUC=0.80) (D). Expression of hsa-miR-19b-3p in plasma of women whose cervix shortened to <25 mm (n=17) compared with those who did not exhibit cervical shortening (n=15), measured using RT PCR (E) at time point C (19-21$^{+6}$ weeks gestation) (TPC). ROC curve showing sensitivity and specificity of hsa-miR-19b-3p to predict cervical shortening at TPC (AUC=0.73) (F). Fold change of hsa-miR-19b-3p expression at each time point, in plasma of women who exhibited cervical shortening compared with expression in women who had normal cervical lengths (G). Fold change increases with gestation.
Figure 5:
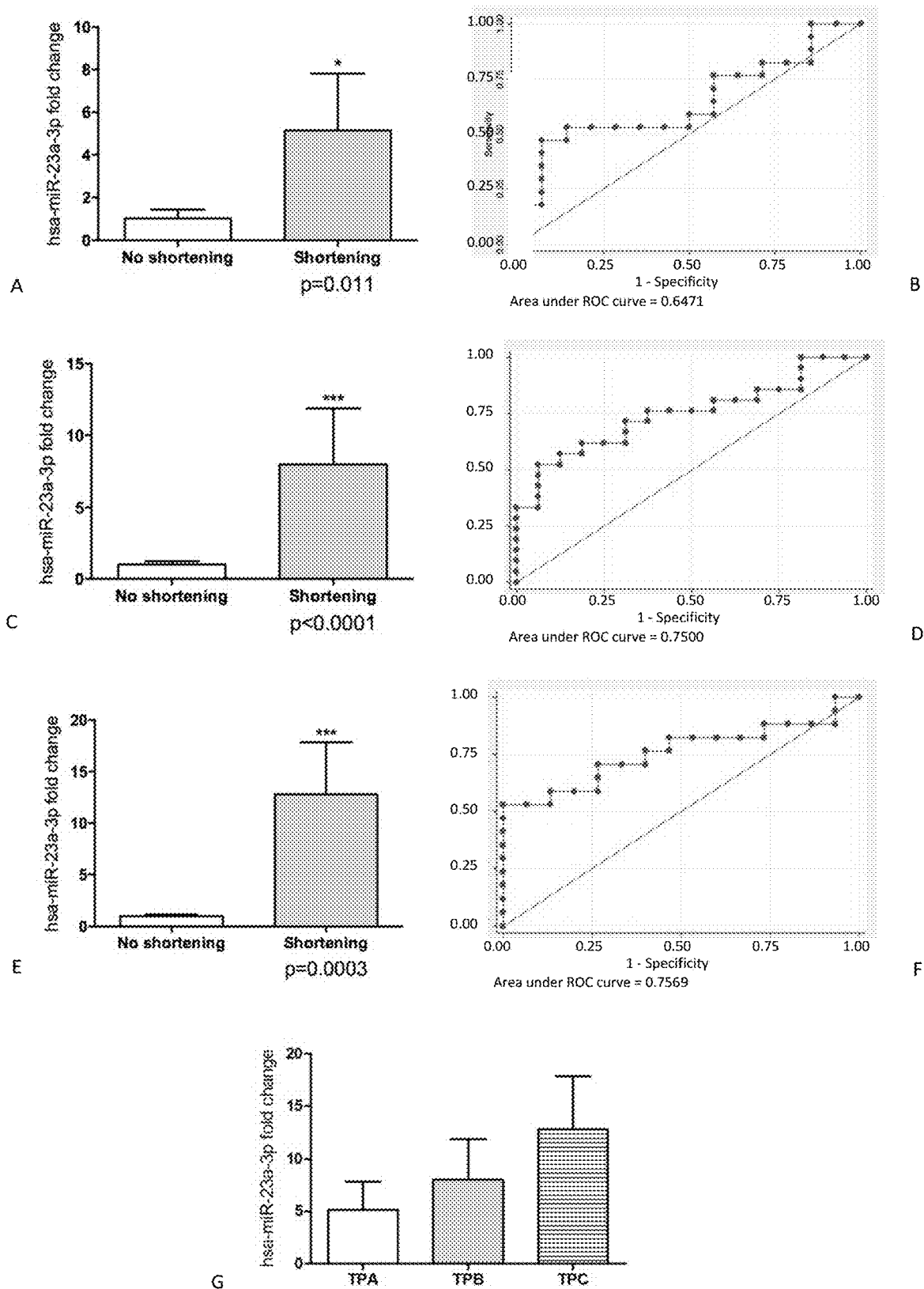
FIG. 5 relates to hsa-miR-23a-3p as a predictor of cervical shortening. Expression of hsa-miR-23a-3p in plasma of women whose cervix shortened to <25 mm (n=18) compared with those who did not exhibit cervical shortening (n=15), measured via real time polymerase chain reaction (RT PCR) at time point A (12-14$^{+6}$ weeks gestation) (TPA) (A). Receiver operated characteristic (ROC) curve showing sensitivity and specificity of hsa-miR-23a-3p to predict cervical shortening at TPA (B) following PCR analysis (AUC=0.65). Expression of hsa-miR-23a-3p in plasma of women whose cervix shortened to <25 mm (n=21) compared with those who did not exhibit cervical shortening (n=16), measured using RT PCR at time point B (15-17$^{+6}$ weeks gestation) (TPB) (C). ROC curve showing sensitivity and specificity of hsa-miR-23a-3p to predict cervical shortening at TPB (AUC=0.75) (D). Expression of hsa-miR-23a-3p in plasma of women whose cervix shortened to <25 mm (n=17) compared with those who did not exhibit cervical shortening (n=15), measured using RT PCR (E) at time point C (19-21$^{+6}$ weeks gestation) (TPC). ROC curve showing sensitivity and specificity of hsa-miR-23a-3p to predict cervical shortening at TPC (AUC=0.76) (F). Fold change of hsa-miR-23a-3p expression at each time point, in plasma of women who exhibited cervical shortening, compared with expression in women who had normal cervical lengths (G). Relative expression of hsa-miR-23a-3p increases with gestation.
Figure 6:
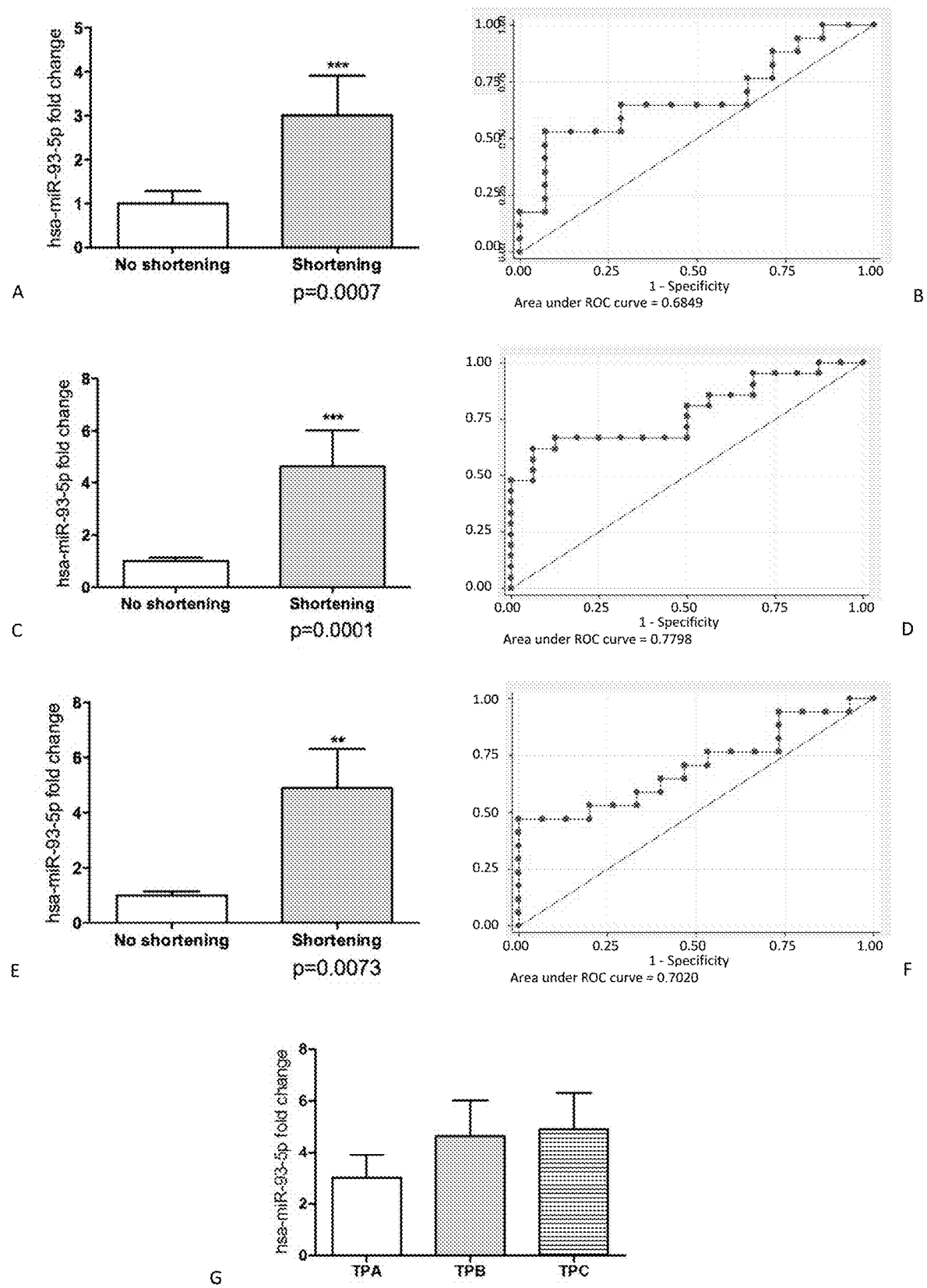
FIG. 6 relates to hsa-miR-93-5p as a predictor of cervical shortening. Expression of hsa-miR-93-5p in plasma of women whose cervix shortened to <25 mm (n=18) compared with those who did not exhibit cervical shortening (n=15), measured via real time polymerase chain reaction (RT PCR) at time point A ($12-14^{+6}$ weeks gestation) (TPA) (A). Receiver operated characteristic (ROC) curve showing sensitivity and specificity of hsa-miR-93-5p to predict cervical shortening at TPA (B) following PCR analysis (AUC=0.68). Expression of hsa-miR-93-5p in plasma of women whose cervix shortened to <25 mm (n=21) compared with those who did not exhibit cervical shortening (n=16), measured using RT PCR at time point B ($15-17^{+6}$ weeks gestation) (TPB) (C). ROC curve showing sensitivity and specificity of hsa-miR-93-5p to predict cervical shortening at TPB (AUC=0.78) (D). Expression of hsa-miR-93-5p in plasma of women whose cervix shortened to <25 mm (n=17) compared with those who did not exhibit cervical shortening (n=15), measured using RT PCR (E) at time point C ($19-21^{+6}$ weeks gestation) (TPC). ROC curve showing sensitivity and specificity of hsa-miR-93-5p to predict cervical shortening at TPC (AUC=0.70) (F). Fold change of hsa-miR-93-5p expression at each time point, in plasma of women who exhibited cervical shortening, compared with expression in women who had normal cervical lengths (G). Relative expression of hsa-miR-93-5p increases with advancing gestation.
Figure 7:
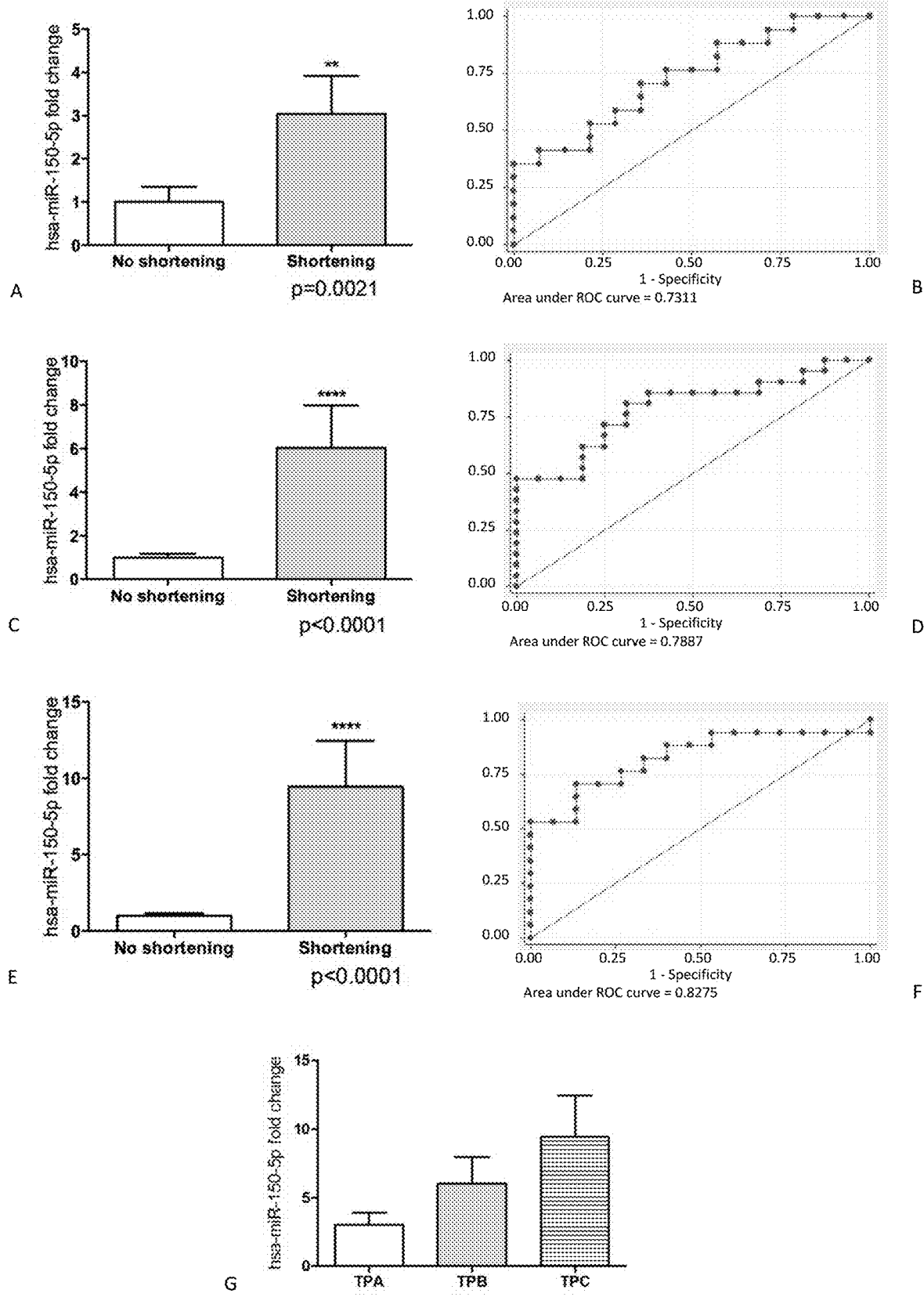
FIG. 7 relates to hsa-miR-150-5p as a predictor of cervical shortening. Expression of hsa-miR-150-5p in plasma of women whose cervix shortened to <25 mm (n=18) compared with those who did not exhibit cervical shortening (n=15), measured via real time polymerase chain reaction (RT PCR) at time point A ($12-14^{+6}$ weeks gestation) (TPA) (A). Receiver operated characteristic (ROC) curve showing sensitivity and specificity of hsa-miR-150-5p to predict cervical shortening at TPA (B) following PCR analysis (AUC=0.73). Expression of hsa-miR-150-5p in plasma of women whose cervix shortened to <25 mm (n=21) compared with those who did not exhibit cervical shortening (n=16), measured using RT PCR at time point B ($15-17^{+6}$ weeks gestation) (TPB) (C). ROC curve showing sensitivity and specificity of hsa-miR-150-5p to predict cervical shortening at TPB (AUC=0.79) (D). Expression of hsa-miR-150-5p in plasma of women whose cervix shortened to <25 mm (n=17) compared with those who did not exhibit cervical shortening (n=15), measured using RT PCR (E) at time point C ($19-21^{+6}$ weeks gestation) (TPC). ROC curve showing sensitivity and specificity of hsa-miR-150-5p to predict cervical shortening at TPC (AUC=0.83) (F). Fold change of hsa-miR-150-5p expression at each time point, in plasma of women who exhibited cervical shortening, compared with expression in women who had normal cervical lengths (G). Relative expression of hsa-miR-150-5p increases with advancing gestation.
Figure 8:
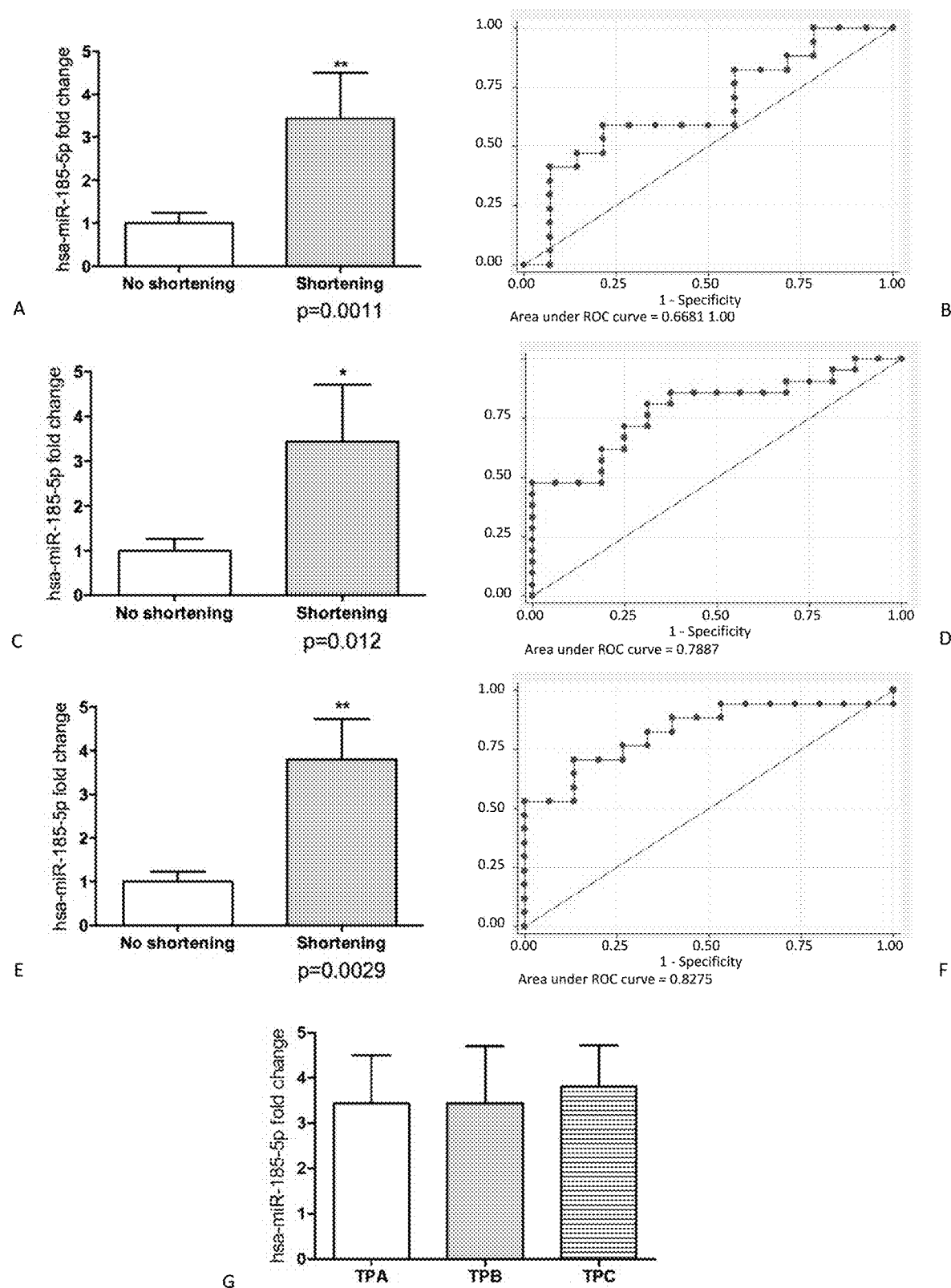
FIG. 8 relates to hsa-miR-185-5p as a predictor of cervical shortening. Expression of hsa-miR-185-5p in plasma of women whose cervix shortened to <25 mm (n=18) compared with those who did not exhibit cervical shortening (n=15), measured via real time polymerase chain reaction (RT PCR) at time point A ($12-14^{+6}$ weeks gestation) (TPA) (A). Receiver operated characteristic (ROC) curve showing sensitivity and specificity of hsa-miR-185-5p to predict cervical shortening at TPA (B) following PCR analysis (AUC=0.67). Expression of hsa-miR-185-5p in plasma of women whose cervix shortened to <25 mm (n=21) compared with those who did not exhibit cervical shortening (n=16), measured using RT PCR at time point B ($15-17^{+6}$ weeks gestation) (TPB) (C). ROC curve showing sensitivity and specificity of hsa-miR-185-5p to predict cervical shortening at TPB (AUC=0.79) (D). Expression of hsa-miR-185-5p in plasma of women whose cervix shortened to <25 mm (n=17) compared with those who did not exhibit cervical shortening (n=15), measured using RT PCR (E) at time point C ($19-21^{+6}$ weeks gestation) (TPC). ROC curve showing sensitivity and specificity of hsa-miR-185-5p to predict cervical shortening at TPC (AUC=0.83) (F). Fold change of hsa-miR-185-5p expression at each time point, in plasma of women who exhibited cervical shortening, compared with expression in women who had normal cervical lengths (G). The increased relative expression of hsa-miR-185-5p does not alter with advancing gestation.
Figure 9:
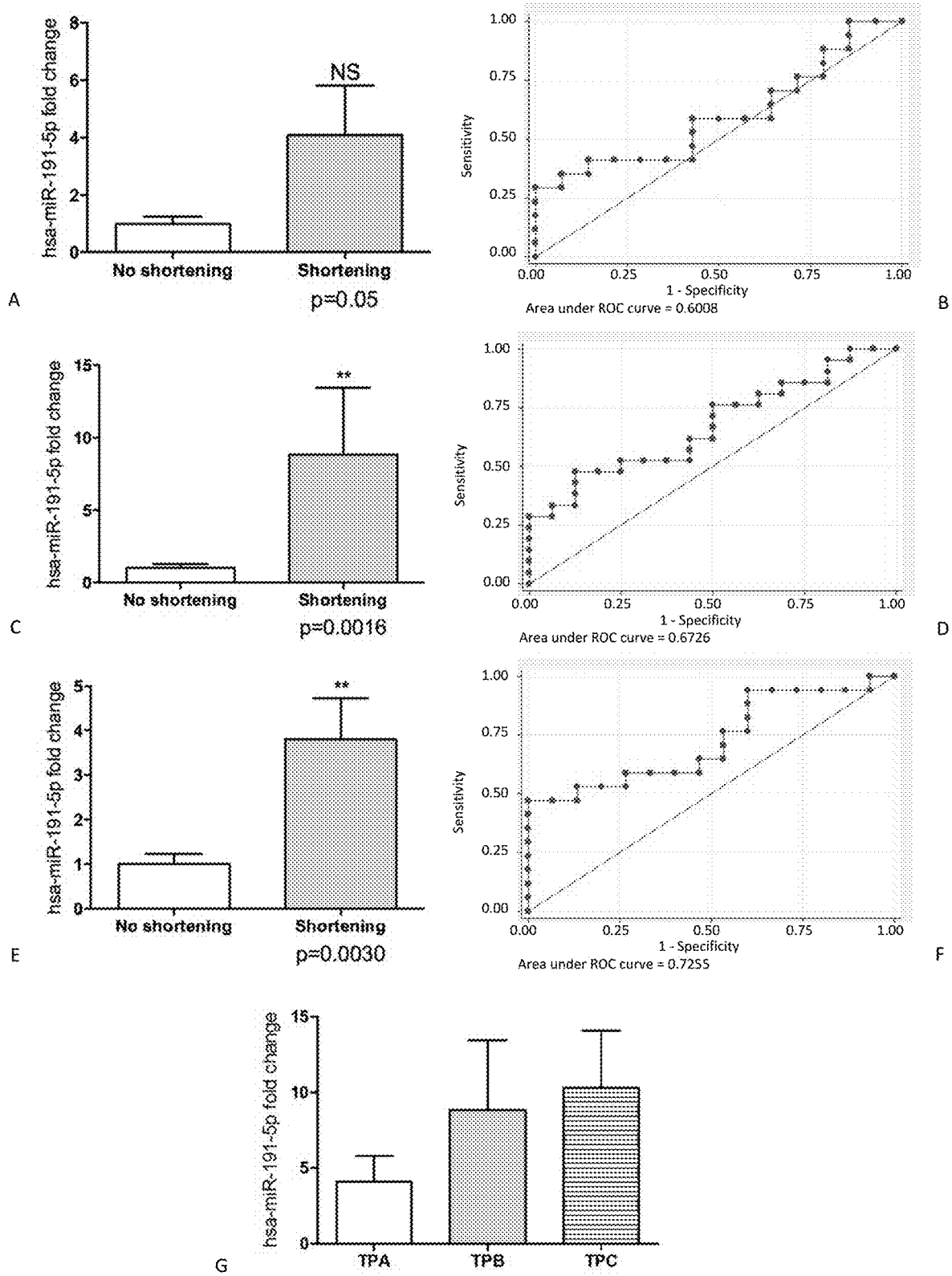
FIG. 9 relates to hsa-miR-191-5p as a predictor of cervical shortening. Expression of hsa-miR-191-5p in plasma of women whose cervix shortened to <25 mm (n=18) compared with those who did not exhibit cervical shortening (n=15), measured via real time polymerase chain reaction (RT PCR) at time point A ($12-14^{+6}$ weeks gestation) (TPA) (A). Receiver operated characteristic (ROC) curve showing sensitivity and specificity of hsa-miR-191-5p to predict cervical shortening at TPA (B) following PCR analysis (AUC=0.60). Expression of hsa-miR-191-5p in plasma of women whose cervix shortened to <25 mm (n=21) compared with those who did not exhibit cervical shortening (n=16), measured using RT PCR at time point B ($15-17^{+6}$ weeks gestation) (TPB) (C). ROC curve showing sensitivity and specificity of hsa-miR-191-5p to predict cervical shortening at TPB (AUC=0.67) (D). Expression of hsa-miR-191-5p in plasma of women whose cervix shortened to <25 mm (n=17) compared with those who did not exhibit cervical shortening (n=15), measured using RT PCR (E) at time point C ($19-21^{+6}$ weeks gestation) (TPC). ROC curve showing sensitivity and specificity of hsa-miR-191-5p to predict cervical shortening at TPC (AUC=0.73) (F). Fold change of hsa-miR-191-5p expression at each time point, in plasma of women who exhibited cervical shortening, compared with expression in women who had normal cervical lengths (G). Relative expression of hsa-miR-191-5p increases with advancing gestation.
Figure 10:
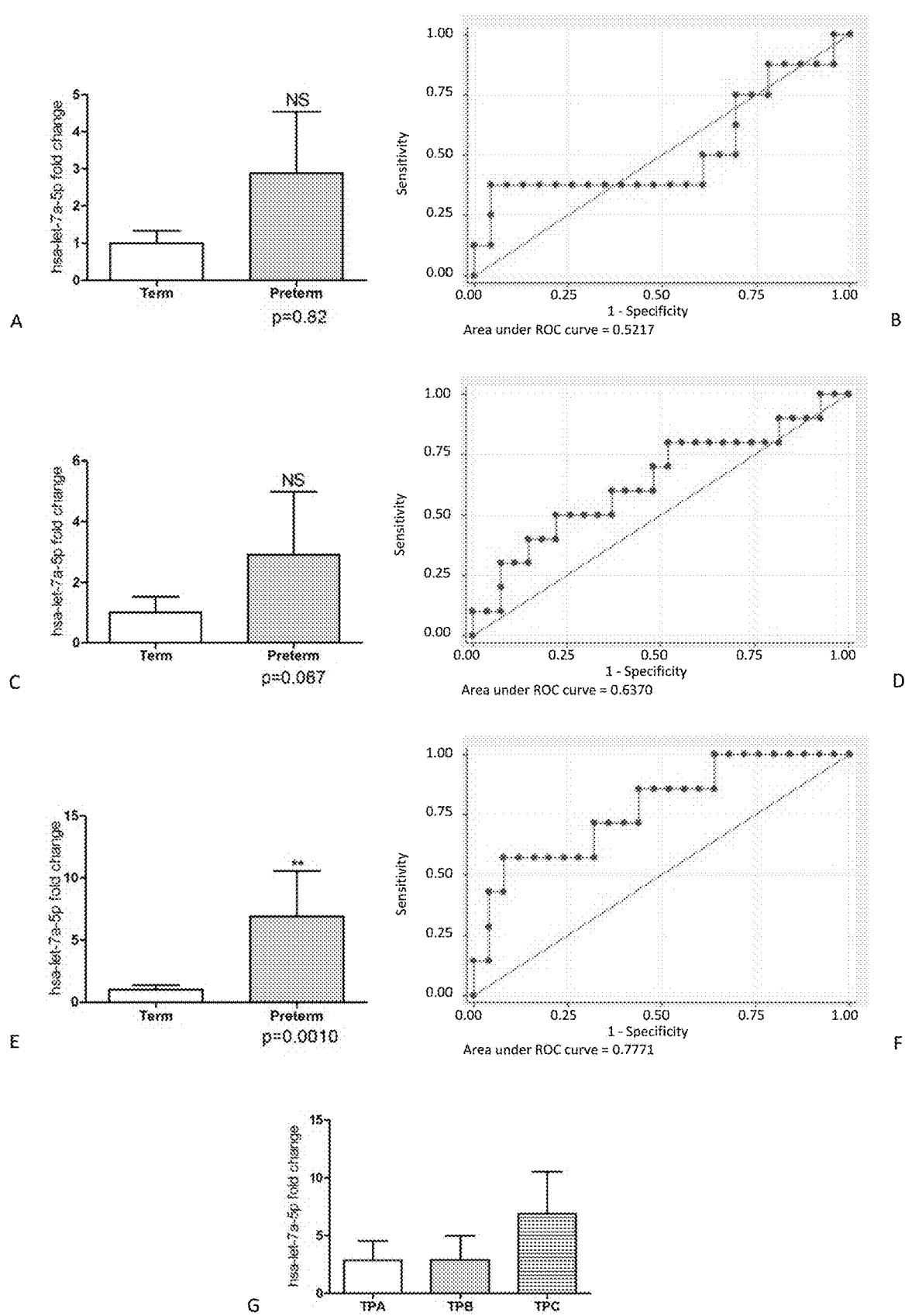
FIG. 10 relates to hsa-let-7a-5p as a predictor of preterm birth. Expression of hsa-let-7a-5p in plasma of women who delivered prior to 34 weeks gestation (n=8) compared with those who delivered at term (n=25), measured via real time polymerase chain reaction (RT PCR) at time point A ($12-14^{+6}$ weeks gestation) (TPA) (A). Receiver operated characteristic (ROC) curve showing sensitivity and specificity of hsa-let-7a-5p to predict preterm birth at TPA following PCR analysis (AUC=0.52) (B). Expression of hsa-let-7a-5p in plasma of women who delivered prior to 34 weeks gestation (n=10) compared with those who delivered at term (n=27), measured using RT PCR at time point B ($15-17^{+6}$ weeks gestation) (TPB) (C). ROC curve showing sensitivity and specificity of hsa-let-7a-5p to predict preterm birth at TPB (AUC=0.64) (D). Expression of hsa-let-7a-5p in plasma of women who delivered prior to 34 weeks gestation (n=7) compared with those who delivered at term (n=25), measured using RT PCR at time point C ($19-21^{+6}$ weeks gestation) (TPC) (E). ROC curve showing sensitivity and specificity of hsa-let-7a-5p to predict preterm birth at TPC (AUC=0.0.78) (F). Fold change of hsa-let-7a-5p expression at each time point, in plasma of women who delivered prior to 34 weeks gestation, compared with expression in women who delivered at term (G). Relative expression of hsa-let-7a-5p increases at TPC.
Figure 11:
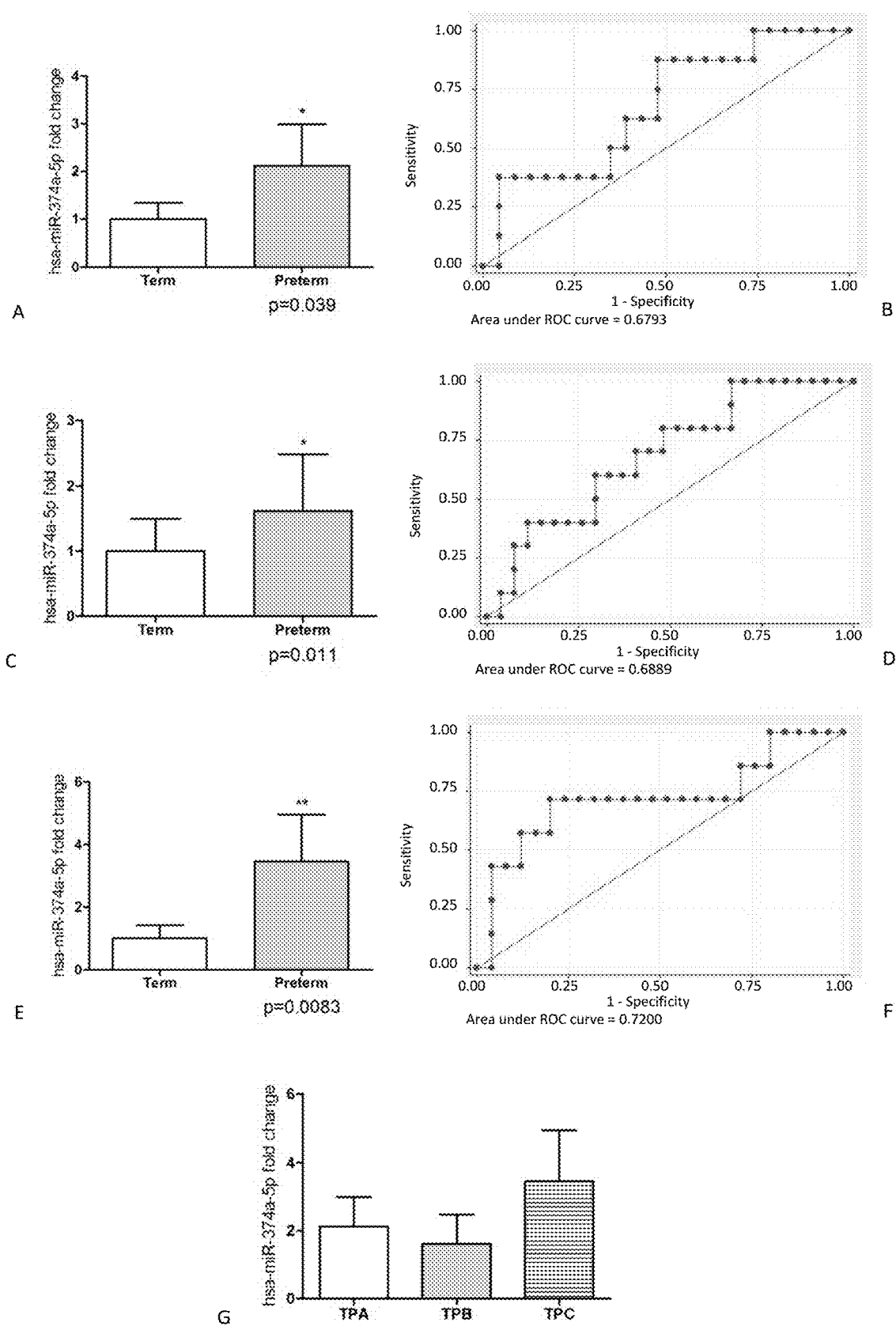
FIG. 11 relates to hsa-miR-374a-5p as a predictor of preterm birth. Expression of hsa-miR-374a-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-374a-5p to predict preterm birth at TPA following PCR analysis (AUC=0.68) (B). Expression of hsa-miR-374a-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-374a-5p to predict preterm birth at TPB (AUC=0.69) (D). Expression of hsa-miR-374a-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-374a-5p to predict preterm birth at TPC (AUC=0.0.72) (F). Fold change of hsa-miR-374a-5p expression at each time point, in plasma of women who delivered prior to 34 weeks gestation, compared with expression in women who delivered at term (G). Relative expression of hsa-miR-374a-5p increases at TPC.
Figure 12:
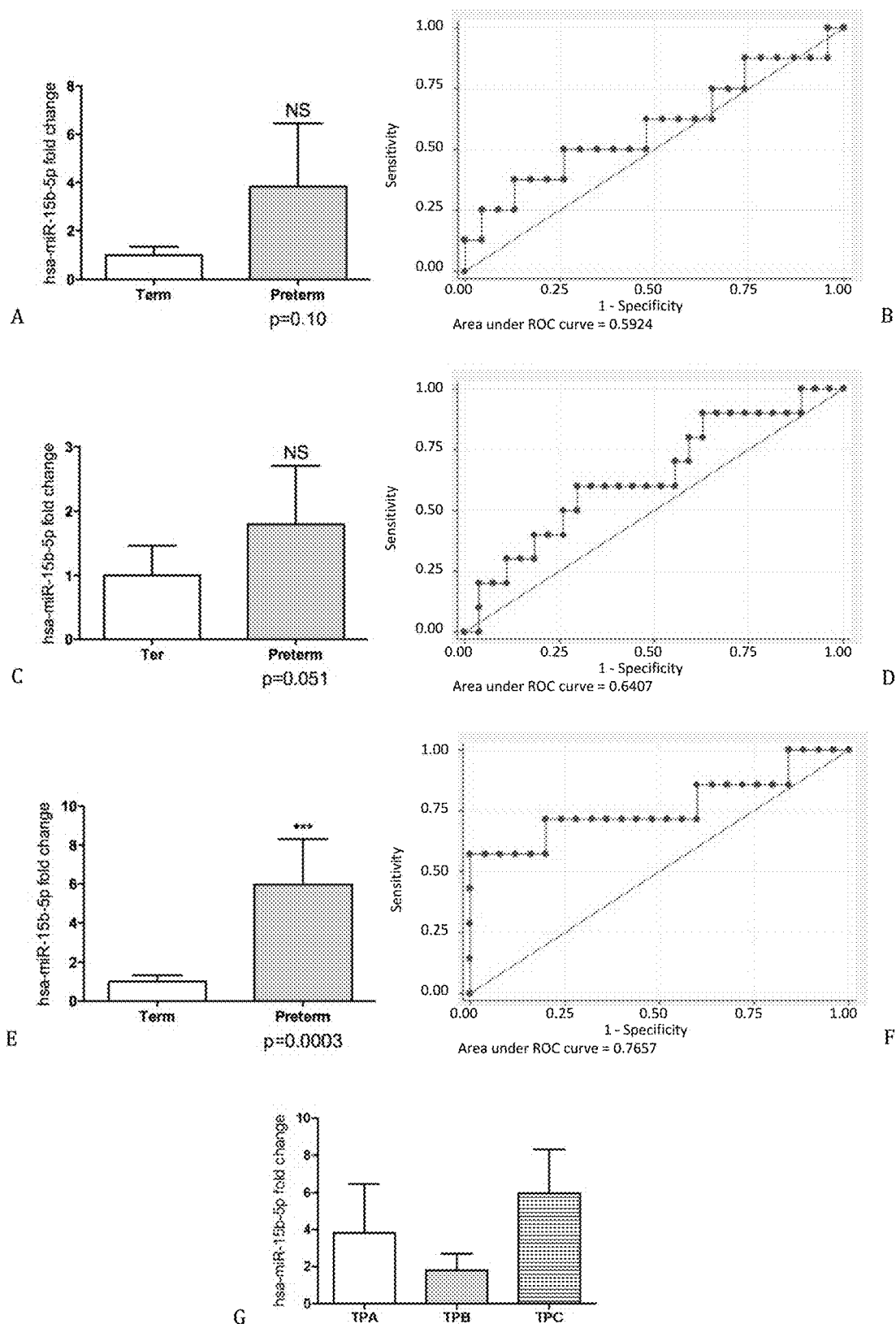
FIG. 12 relates to hsa-miR-15b-5p as a predictor of preterm birth. Expression of hsa-miR-15b-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-15b-5p to predict preterm birth at TPA following PCR analysis (AUC=0.59) (B). Expression of hsa-miR-15b-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-15b-5p to predict preterm birth at TPB (AUC=0.64) (D). Expression of hsa-miR-15b-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-15b-5p to predict preterm birth at TPC (AUC=0.0.77) (F). Fold change of hsa-miR-15b-5p expression at each time point, in plasma of women who delivered prior to 34 weeks gestation, compared with expression in women who delivered at term (G). Relative expression of hsa-miR-15b-5p is greatest at TPA and TPC.
Figure 13:
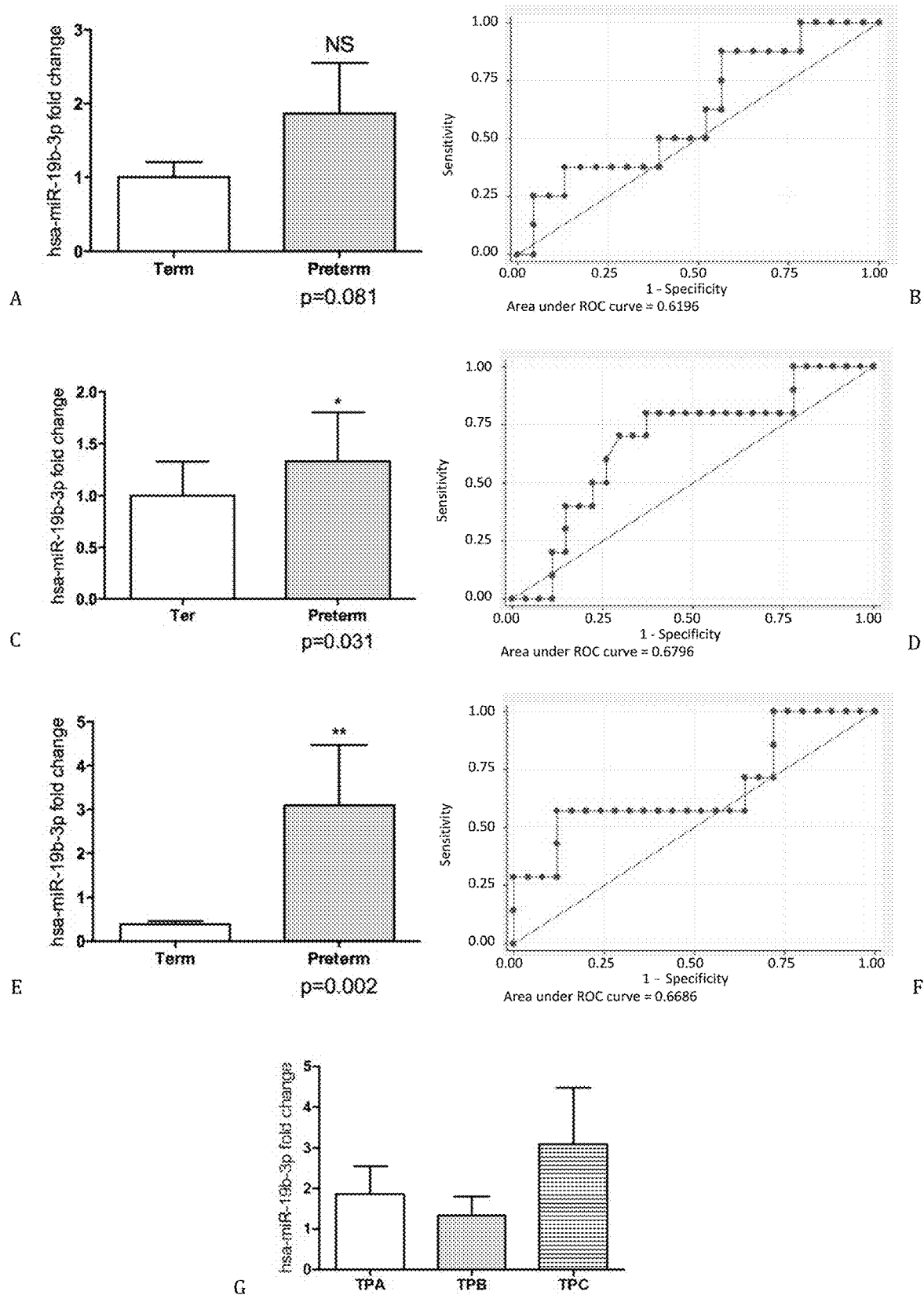
FIG. 13 relates to hsa-miR-19b-5p as a predictor of preterm birth. Expression of hsa-miR-19b-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-19b-5p to predict preterm birth at TPA following PCR analysis (AUC=0.62) (B). Expression of hsa-miR-19b-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-19b-5p to predict preterm birth at TPB (AUC=0.68) (D). Expression of hsa-miR-19b-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-19b-5p to predict preterm birth at TPC (AUC=0.0.67) (F). Fold change of hsa-miR-19b-5p expression at each time point, in plasma of women who delivered prior to 34 weeks gestation, compared with expression in women who delivered at term (G). Relative expression of hsa-miR-19b-5p is greatest at TPA and TPC.
Figure 14:
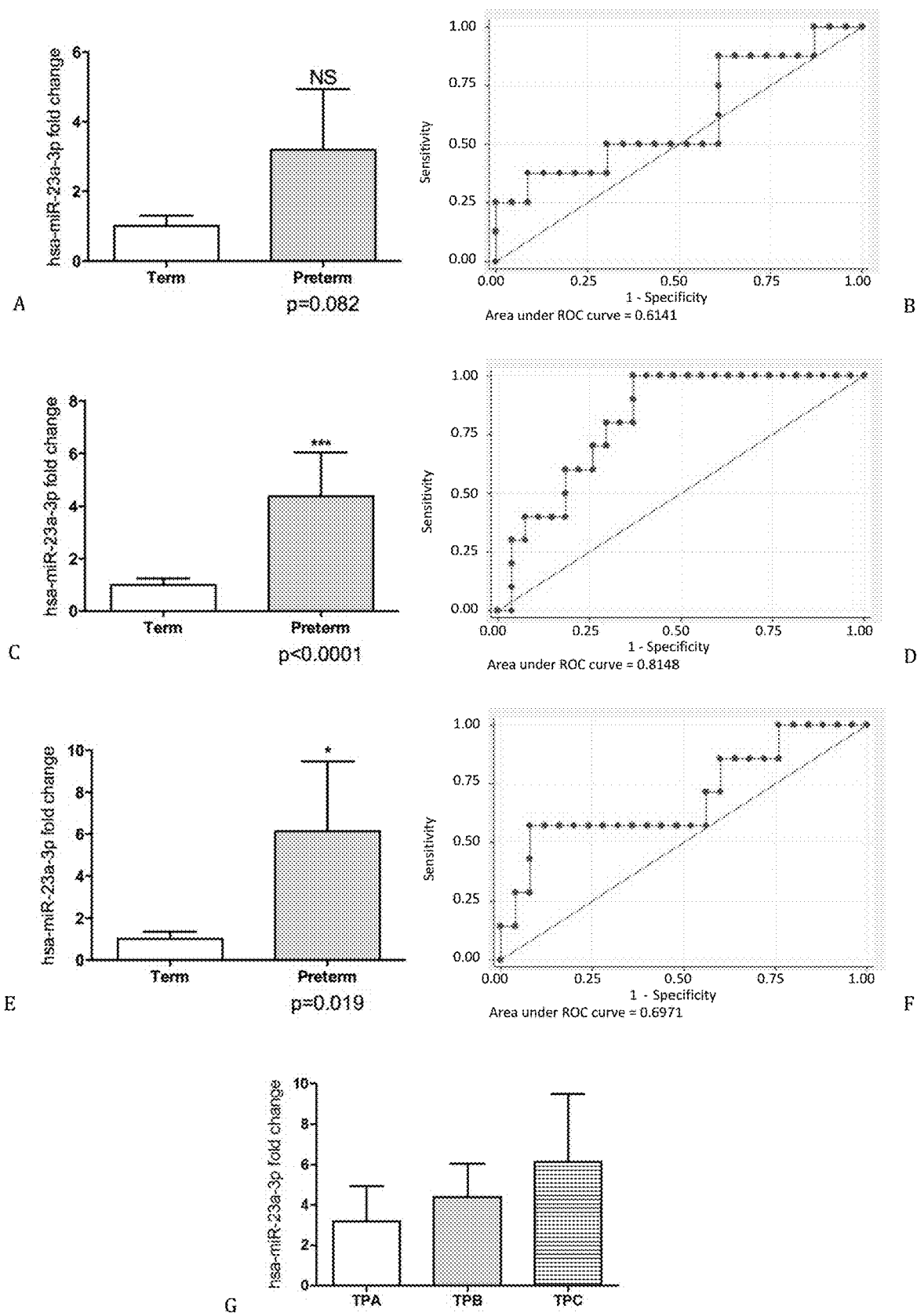
FIG. 14 relates to hsa-miR-23a-3p as a predictor of preterm birth. Expression of hsa-miR-23a-3p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-23a-3p to predict preterm birth at TPA following PCR analysis (AUC=0.61) (B). Expression of hsa-miR-23a-3p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-23a-3p to predict preterm birth at TPB (AUC=0.81) (D). Expression of hsa-miR-23a-3p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-23a-3p to predict preterm birth at TPC (AUC=0.70) (F). Fold change of hsa-miR-23a-3p expression at each time point, in plasma of women who delivered prior to 34 weeks gestation, compared with expression in women who delivered at term (G). Relative expression of hsa-miR-23a-3p increases with advancing gestation.
Figure 15:
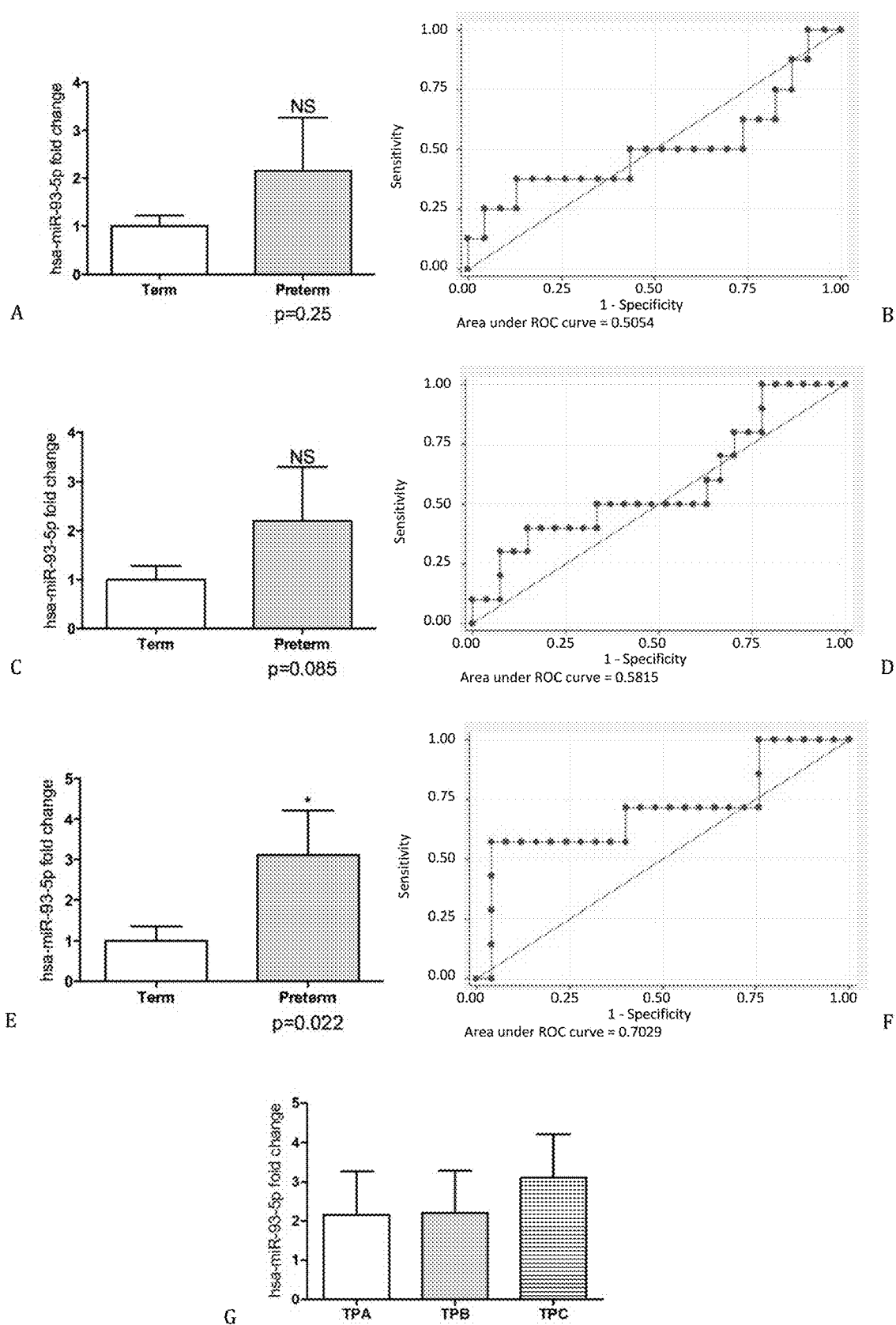
FIG. 15 relates to hsa-miR-93-5p as a predictor of preterm birth. Expression of hsa-miR-93-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-93-5p to predict preterm birth at TPA following PCR analysis (AUC=0.51) (B). Expression of hsa-miR-93-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-93-5p to predict preterm birth at TPB (AUC=0.58) (D). Expression of hsa-miR-93-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-93-5p to predict preterm birth at TPC (AUC=0.70) (F). Fold change of hsa-miR-93-5p expression at each time point, in plasma of women who delivered prior to 34 weeks gestation, compared with expression in women who delivered at term (G). Relative expression of hsa-miR-93-5p is greatest at TPC.
Figure 16:
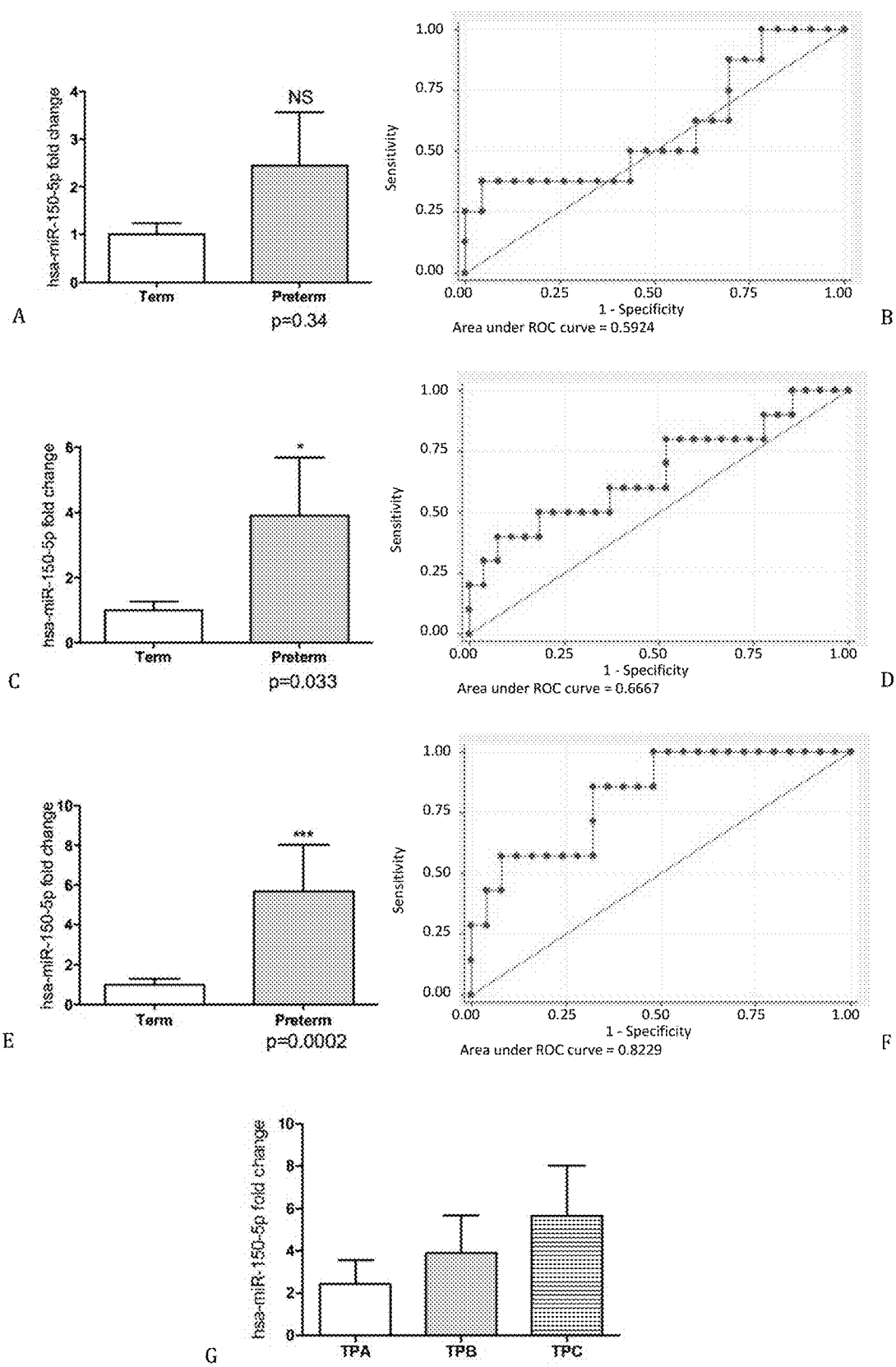
FIG. 16 relates to hsa-miR-150-5p as a predictor of preterm birth. Expression of hsa-miR-150-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-150-5p to predict preterm birth at TPA following PCR analysis (AUC=0.59) (B). Expression of hsa-miR-150-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-150-5p to predict preterm birth at TPB (AUC=0.67) (D). Expression of hsa-miR-150-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-150-5p to predict preterm birth at TPC (AUC=0.82) (F). Fold change of hsa-miR-150-5p expression at each time point, in plasma of women who delivered prior to 34 weeks gestation, compared with expression in women who delivered at term (G). Relative expression of hsa-miR-150-5p increases with advancing gestation.
Figure 17:
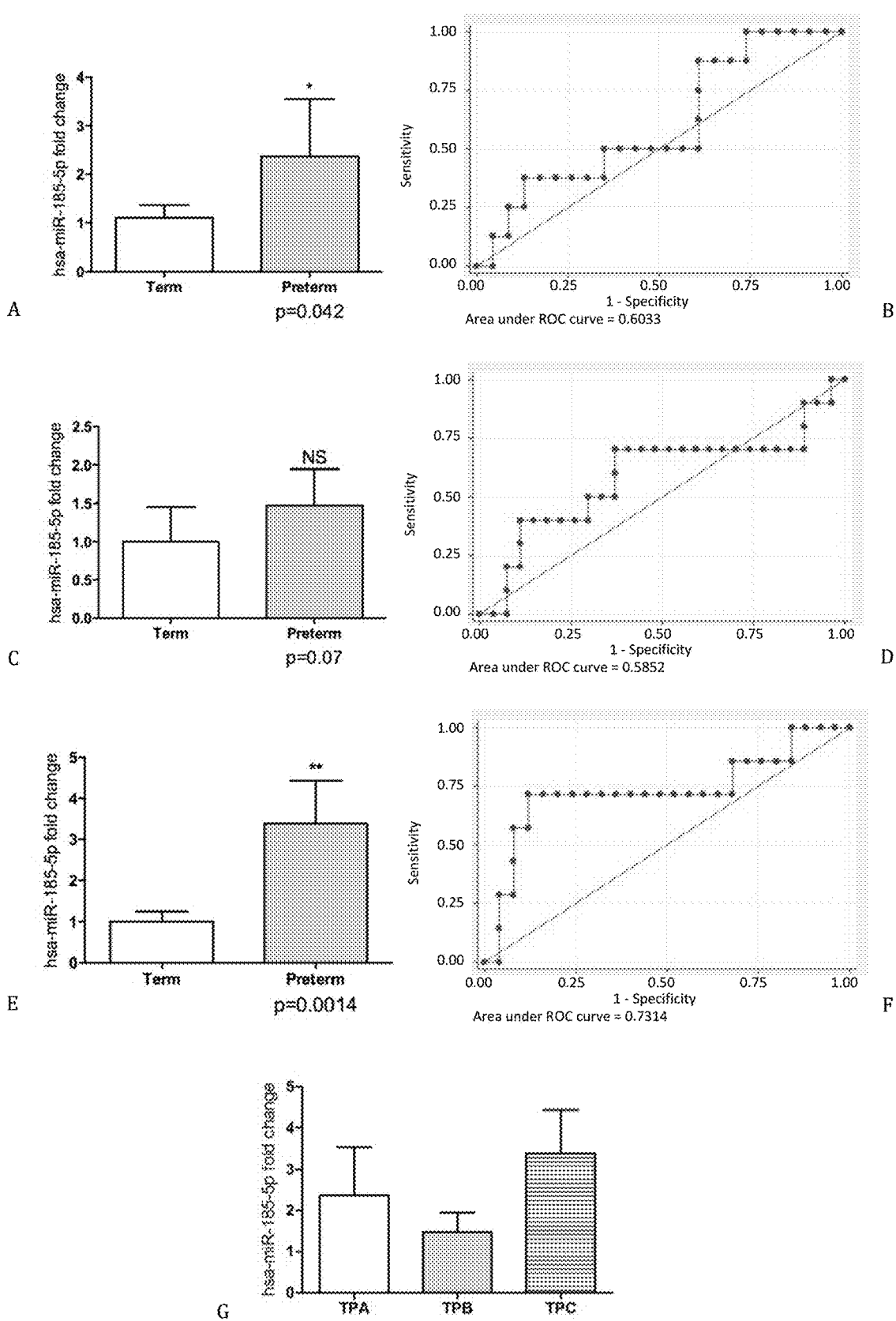
FIG. 17 relates to hsa-miR-185-5p as a predictor of preterm birth. Expression of hsa-miR-185-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-185-5p to predict preterm birth at TPA following PCR analysis (AUC=0.60) (B). Expression of hsa-miR-185-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-185-5p to predict preterm birth at TPB (AUC=0.59) (D). Expression of hsa-miR-185-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-185-5p to predict preterm birth at TPC (AUC=0.73) (F). Fold change of hsa-miR-185-5p expression at each time point, in plasma of women who delivered prior to 34 weeks gestation, compared with expression in women who delivered at term (G). Relative expression of hsa-miR-185-5p is greatest at TPC.
Figure 18:
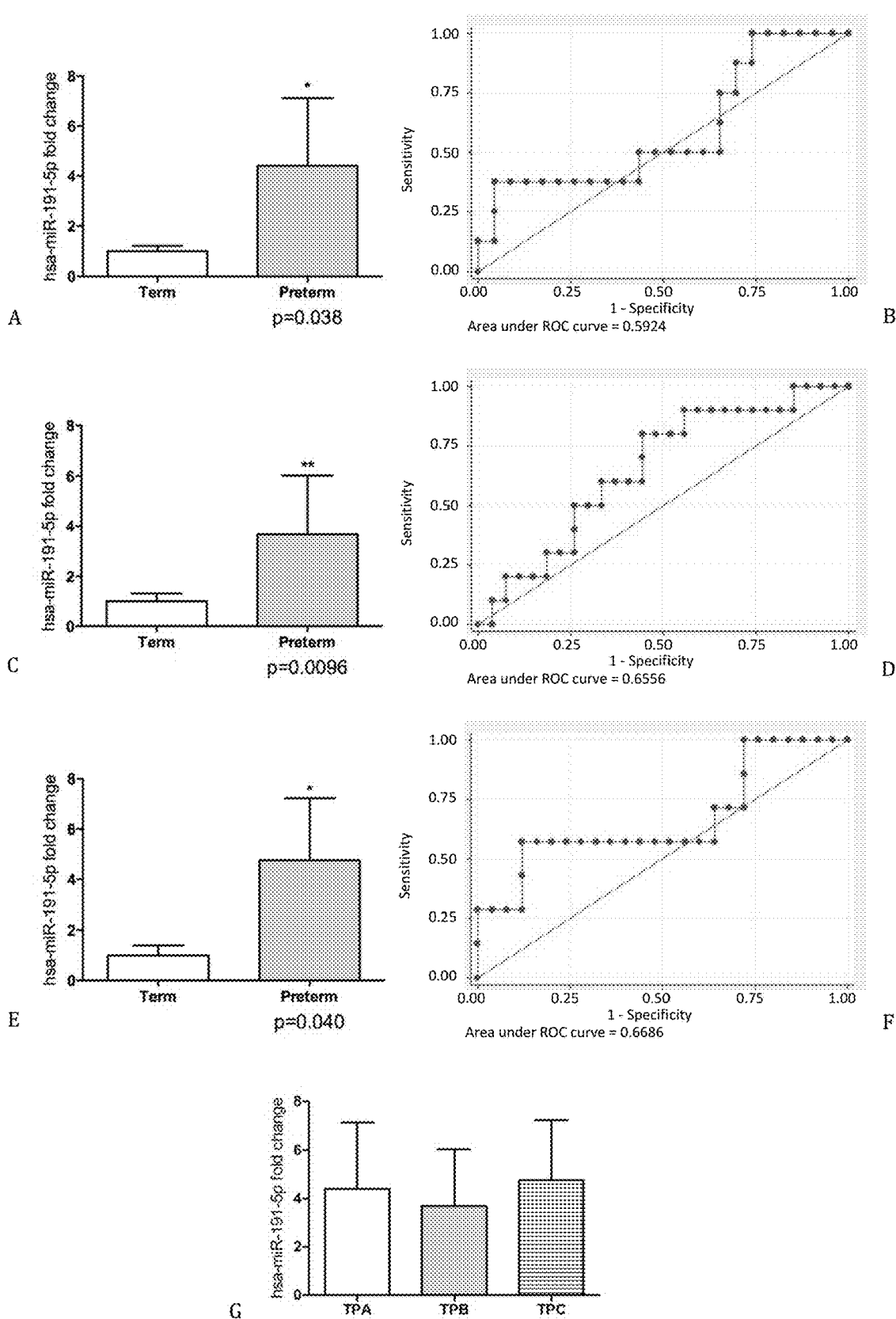
FIG. 18 relates to hsa-miR-191-5p as a predictor of preterm birth. Expression of hsa-miR-191-5p in plasma of women who delivered prior to 34 weeks gestation (n=8) compared with those who delivered at term (n=25), measured via real time polymerase chain reaction (RT PCR) at time point A (12-14$^{+6}$ weeks gestation) (TPA) (A). Receiver operated characteristic (ROC) curve showing sensitivity and specificity of hsa-miR-191-5p to predict preterm birth at TPA following PCR analysis (AUC=0.59) (B). Expression of hsa-miR-191-5p in plasma of women who delivered prior to 34 weeks gestation (n=10) compared with those who delivered at term (n=27), measured using RT PCR at time point B (15-17$^{+6}$ weeks gestation) (TPB) (C). ROC curve showing sensitivity and specificity of hsa-miR-191-5p to predict preterm birth at TPB (AUC=0.66) (D). Expression of hsa-miR-191-5p in plasma of women who delivered prior to 34 weeks gestation (n=7) compared with those who delivered at term (n=25), measured using RT PCR at time point C (19-21$^{+6}$ weeks gestation) (TPC) (E). ROC curve showing sensitivity and specificity of hsa-miR-191-5p to predict preterm birth at TPC (AUC=0.67) (F). Fold change of hsa-miR-185-5p expression at each time point, in plasma of women who delivered prior to 34 weeks gestation, compared with expression in women who delivered at term (G). Relative expression of hsa-miR-185-5p is higher at all three time points, in women who go on to deliver preterm.
Figure 19:
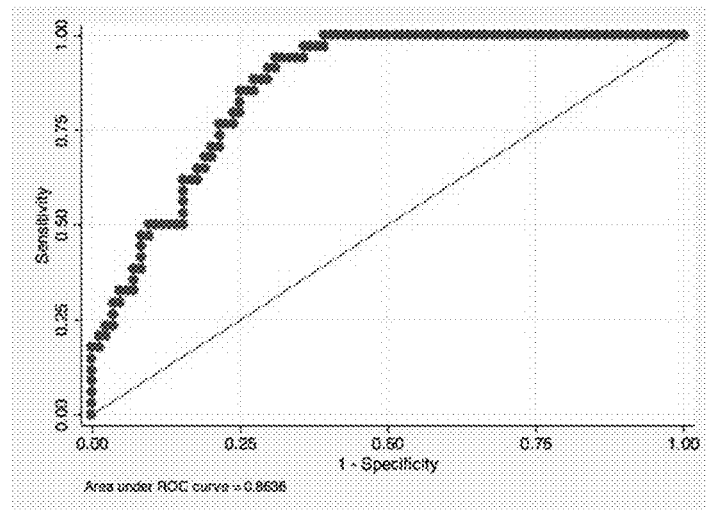
FIG. 19 shows a receiver operator characteristic curve describing the ability of plasma hsa-miR-150-5p to predict cervical shortening at 12-14$^{+6}$ weeks gestation (AUC=0.86).

The present invention is based upon the surprising discovery of a group of miRNA molecules which are present in the maternal circulation and whose concentration in the circulation predicts subsequent cervical shortening. For each of the miRNA molecules identified herein, the concentration of miRNA in the maternal circulation is altered in women whose cervix subsequently shortens. Advantageously, expression levels of theses miRNA can be measured from blood samples which can be obtained from woman in the early stages of pregnancy (from gestation week 12 onwards), thereby providing a minimally-invasive means for early detection/prediction of cervical shortening, which can lead to preterm labour.

Therefore, the first aspect of the invention provides a method for predicting risk of cervical shortening in a pregnant female subject, comprising determining the expression level of one or more of the miRNA molecules identified in Table 1 or Table 2 extracted from a biological sample obtained from said subject and comparing to a control value, wherein a difference in the expression level of the one or more of the miRNA molecules compared to the control value indicates that the subject is at high or low risk of cervical shortening.

If the miRNA molecule that is detected using the method according to this aspect of the invention is a molecule whose over-expression is associated with increased risk of cervical shortening (this includes each of the miRNAs identified in Table 1), then an elevated expression level of said miRNA in the patient's sample compared to the control value is indicative of high risk of cervical shortening in said patient.

If the miRNA molecule that is detected using the method according to this aspect of the invention is a molecule whose under-expression is associated with increased risk of cervical shortening, then an expression level of said miRNA in the patient's sample that is lower than the control value is indicative of high risk of cervical shortening in said patient.

The direction of change of the difference in expression compared to the control value (i.e. elevated or decreased expression) that is indicative of high risk of cervical shortening for each of the miRNAs of the invention is indicated in the final column of Tables 1 and 2.

For all of the miRNAs listed in Table 1, and all of the miRNAs listed in Table 2 except for hsa-miR-188-5p, an elevated expression level of the miRNA molecule compared to the control value indicates that the subject is at high risk of cervical shortening.

For the miRNA hsa-miR-188-5p (Table 2) a decrease in the expression level of the miRNA molecule compared to the control value indicates that the subject is at high risk of cervical shortening.

If, as a result of carrying out the method of the invention, the patient is identified as being at high risk of cervical shortening, then further diagnostic testing or monitoring such as ultrasound screening of cervical length could be offered. If the cervix is found to be short the patient can be treated with therapeutic interventions.

Suitable therapeutic interventions include administering one or more of: oxytocin receptor antagonists, prostaglandin receptor antagonists, beta-adrenergic receptor agonists, nitrogen oxide donors, magnesium sulphate, prostaglandin-synthase inhibitors, non-steroidal anti-inflammatory drugs (NSAIDs), small molecule and other anti-inflammatory drugs, calcium channel blockers, progesterone, 17-a-hydroxyprogesterone caproate, and progesterone analogues. The patient may additionally or alternatively be treated with surgical intervention such as cervical cerclage.

No difference in the expression level of said miRNA molecule in the patient's sample compared with the control value, or change in the expression level of said miRNA molecule compared with the control value in opposite direction to that which is indicative of risk of cervical shortening for said miRNA, indicates that the subject is at low risk of cervical shortening. If the subject is identified as being at low risk of cervical shortening then further diagnostic testing and/or therapeutic or surgical interventions such as those described herein are unlikely to be required. As used herein, the term "cervical shortening" (also referred to as "cervical ripening") refers to change (i.e. reduction) in the length of the cervix that occurs during pregnancy. Cervical shortening to a length of around 25 mm or less is a cause of pregnancy loss and early preterm delivery, and despite preventative treatment, about 50% of women whose cervix shortens will go on to delivery preterm.

The group of miRNA markers identified by the present inventors can also be used to determine risk of a pregnant subject suffering preterm labour (PTL).

As such, a second aspect of the invention provides a method for predicting risk of PTL in a pregnant subject, comprising determining the expression level of one or more miRNA molecules identified in Table 1 or Table 2 extracted from a biological sample obtained from said subject and comparing to a control value, wherein a difference in the expression level of the one or more of the miRNA molecules compared to the control value indicates that the subject is at high or low risk of PTL.

If the miRNA molecule that is detected using the method according to this aspect of the invention is a molecule whose over-expression is associated with increased risk of PTL, then an expression level of said miRNA in the patient's sample that is elevated compared with the control value is indicative of high risk of PTL in said patient.

If the miRNA molecule that is detected using the method according to this aspect of the invention is a molecule whose under-expression is associated with increased risk of PTL, then an expression level of said miRNA in the patient's sample that is lower than the control value is indicative of high risk of PTL in said patient.

If, as a result of carrying out the method of the invention, the patient is identified as being at high risk of PTL, then further diagnostic testing or monitoring can be carried out and/or the patient can be treated with therapeutic interventions, which aim to prevent a preterm birth. Suitable therapeutic interventions include administering one or more of: oxytocin receptor antagonists, prostaglandin receptor antagonists, beta-adrenergic receptor agonists, nitrogen oxide donors, magnesium sulphate, prostaglandin-synthase inhibitors, non-steroidal anti-inflammatory drugs (NSAIDs), small molecule and other anti-inflammatory drugs, calcium channel blockers, progesterone, 17-a-hydroxyprogesterone caproate, and progesterone analogues. The patient may additionally or alternatively be treated with surgical intervention, such as cervical cerclage.

The direction of change of the difference in expression compared to the control value that is indicative of high risk of PTL for each of the miRNAs of the invention is indicated in the final column of Tables 1 and 2. For all of the miRNAs listed in Table 1, and all of the miRNAs listed in Table 2 except for hsa-miR-188-5p, an elevated expression level of the miRNA molecule compared to the control value indicates that the subject is at high risk of PTL. For the miRNA hsa-miR-188-5p (Table 2) a decrease in the expression level of the miRNA molecule compared to the control value indicates that the subject is at high risk of PTL.

No difference in the expression level of said miRNA molecule in the patient's sample compared with the control value, or difference in the expression level of said miRNA molecule compared with the control value in opposite direction to that which is indicative of risk of PTL for said miRNA, indicates that the subject is at low risk of PTL. If, as a result of carrying out the method of the invention, the subject is identified as being at low risk of PTL then further diagnostic testing or monitoring and/or therapeutic interventions are unlikely to be required.

The term "preterm labour (PTL)" refers to the condition where labour begins three or more weeks before the full gestation period of about 40 weeks (i.e. labour begins at 37 weeks of gestation or less). PTL can lead to a premature (or preterm) birth.

The term "high risk" refers to a level of risk of cervical shortening or PTL whereby further diagnostic testing, monitoring of the patient or therapeutic intervention is appropriate. The term "low risk" refers to a level of risk of cervical shortening or PTL whereby further diagnostic testing, monitoring of the patient or therapeutic or surgical intervention is unlikely to be necessary.

As used herein, the term "therapeutic intervention" refers to treating a patient by administering one or more drugs. The term "surgical intervention" refers to performing a surgical procedure on the patient.

The methods of the first and second aspects of the invention can be applied to a general low risk obstetric population, in order to identify risk of cervical shortening and/or PTL in women who have no medical history that would indicate that they are at risk of cervical shortening and/or PTL, and who would otherwise not be placed under surveillance or receive any therapeutic or surgical intervention to prevent cervical shortening and/or PTL.

Alternatively, the methods of the invention can be applied to a high risk obstetric population, comprising pregnant women who do have a significant personal medical history including one or more of previous PTL, mid-trimester loss or cervical cone biopsy, which would indicate that they are at risk of cervical shortening and/or PTL.

All women who demonstrate cervical shortening are offered some sort of preventative treatment (usually either cervical cerclage or drug therapy such as progesterone), and so the same group of miRNA markers that have been identified by the present inventors are also useful for predicting the need for therapeutic intervention. This is particularly useful in the context of differentiating between pregnant subjects who have a history of previous PTL, mid-trimester loss or cervical cone biopsy and are in need of cervical ultrasound screening, cervical cerclage and/or progesterone therapy, and those who have a background history that puts them at risk of PTL but who do not require such treatment or intervention.

Identifying patients in high risk of preterm birth populations whose cervix will not go on to shorten enables them to be eliminated from high intensity surveillance of cervical length. This is advantageous from the patient's perspective, because they are not subject to unnecessary ultrasound screening visits, and also from the perspective of public health service providers, as resources can be used in a more efficient and focused manner.

Therefore, the third aspect of the invention provides a method for characterising a pregnant subject having a history of previous PTL, mid-trimester loss or cervical cone biopsy as being in need of cervical ultrasound screening, and potentially therapeutic or surgical intervention, comprising determining the expression level of one or more miRNA molecules identified in Table 1 or Table 2 extracted from a biological sample obtained from said subject and comparing to a control value, wherein a difference in the expression level compared with the control value indicates that the subject is in need of cervical ultrasound screening, and potentially therapeutic or surgical intervention.

If the miRNA molecule that is detected using the method according to this aspect of the invention is a molecule whose over-expression is associated with increased risk of cervical shortening and/or PTL, then an expression level of said miRNA in the patient's sample that is elevated compared with the control value is indicative of need for cervical ultrasound screening, therapeutic and/or surgical intervention.

If the miRNA molecule that is detected using the method according to this aspect of the invention is a molecule whose under-expression is associated with increased risk of cervical shortening and/or PTL, then an expression level of said miRNA in the patient's sample that is lower than the control value is indicative of need for cervical ultrasound screening, therapeutic and/or surgical intervention.

If, as a result of carrying out the method of the invention, the patient is identified as being in need of cervical ultrasound screening, therapeutic and/or surgical intervention then such screening and/or therapy and/or surgery can be administered. Suitable therapeutic interventions include administering one or more of: oxytocin receptor antagonists, prostaglandin receptor antagonists, beta-adrenergic receptor agonists, nitrogen oxide donors, magnesium sulphate, prostaglandin-synthase inhibitors, non-steroidal anti-inflammatory drugs (NSAIDs), small molecule and other anti-inflammatory drugs, calcium channel blockers, progesterone, 17-a-hydroxyprogesterone caproate, and progesterone analogues. Suitable surgical intervention includes cervical cerclage.

The direction of change of the difference in expression compared to the control value that is indicative of high risk of cervical shortening and/or PTL for each of the miRNAs of the invention is indicated in the final column of Tables 1 and 2. For all of the miRNAs listed in Table 1, and all of the miRNAs listed in Table 2 except for hsa-miR-188-5p, an elevated expression level of the miRNA molecule compared to the control value indicates that the subject is at high risk of cervical shortening and/or PTL.

For the miRNA hsa-miR-188-5p (Table 2) a decrease in the expression level of the miRNA molecule compared to the control value indicates that the subject is at high risk of cervical shortening and/or PTL.

No difference in the expression level of said miRNA molecule in the patient's sample compared with the control value, or a difference in the expression level of said miRNA molecule compared with the control value in opposite direction to that which is indicative of risk of cervical shortening or PTL for said miRNA, indicates that the subject is not in need of cervical ultrasound screening, therapeutic and/or surgical intervention. In this case, further screening and/or therapy and/or surgery are not required and on the basis of this result a clinician may decide that the patient's pregnancy can proceed without any therapeutic or surgical intervention or monitoring of cervical length.

It will be apparent to the person skilled that the methods of the invention disclosed herein can be used in conjunction with other methods for screening for PTL and determining cervical length that are well known in the art.

The terms "patient" and "subject" are used interchangeably herein and refer to any female animal (e.g. mammal), including, but not limited to, humans, non-human primates, canines, felines, rodents and the like. Preferably, the subject or patient is a human female.

The terms "microRNA", "miRNA" and "miR" are used interchangeably herein and refer to small non-coding RNA molecules.

The methods of the invention described herein are carried out ex vivo. For the avoidance of doubt, the term "ex vivo" has its usual meaning in the art, referring to methods that are carried out in or on a biological sample in an artificial environment outside the body of the patient from whom the biological sample has been obtained.

All references herein to a "biological sample" preferably refer to a blood sample. As used herein, the term "blood sample" includes whole blood and blood components, including plasma and serum. In preferred embodiments, the one or more miRNA molecules are extracted from the plasma component of a whole blood sample or from the serum component of a whole blood sample.

As used herein, "plasma" refers to the fluid portion of blood, excluding blood cells and platelets, but including dissolved proteins, glucose, clotting factors, electrolytes and hormones. As used herein, "serum" refers to blood plasma without clotting factors.

The skilled person will be familiar with standard phlebotomy techniques which are suitable for obtaining a blood sample from a subject. The skilled person will also be familiar with routine techniques for obtaining plasma and/or serum from a whole blood sample, e.g. using centrifugation.

In a preferred embodiment of each of the first, second and third aspects of the invention the methods are carried out using biological samples obtained at between 12 to 24 weeks gestation, preferably at between 12 to 16 weeks gestation (also referred to herein as "time point A"), and/or at between 16 to 18 weeks gestation (also referred to herein as "time point B"), and/or at between 18 to 24 weeks gestation (also referred to herein as "time point C").

As the skilled person will readily understand, references to gestational periods used herein use the standard notation of "number of weeks $^{+6}$", to indicate a number of gestational weeks plus up to 6 days.

In a preferred embodiment of each of the first, second and third aspects of the invention the expression level of a combination of two or more of the miRNA molecules identified in Table 1 or Table 2 or Table 3, and preferably a combination of three or four of the miRNA molecules identified in Table 1 or Table 2 or Table 3 is determined. In a particularly preferred embodiment the expression level of all nine of the miRNAs in Table 1 is determined. In such embodiments of the first, second and third aspects of the invention, the combined expression level of the two, three or four or more miRNA molecules is compared to the control value.

As used herein in relation to the first, second and third aspects of the invention, the term "control value" refers to a baseline expression level of the corresponding miRNA molecule(s) in a corresponding control sample. The corresponding control sample may be obtained from a cohort of pregnant female subjects who reached full-term (>37 weeks gestation) with no cervical shortening.

If the expression level of two or more miRNA molecules is determined in the methods of the invention, the corresponding control value is the combined baseline expression level of the corresponding miRNAs in a control sample.

Preferably, for each of the methods of the invention, the cut-off value for determining whether the expression level of a given miRNA molecule is "different" (elevated or reduced) compared with a control value is 2-times the baseline expression level for the miRNA. Therefore if the expression level of a given miRNA (e.g. hsa-let-7a-5p) is determined and the expression value is found to be at least 2-fold greater than the baseline expression level for hsa-let-7a-5p in a control sample, then it can be concluded that hsa-let-7a-5p expression is elevated in the subject's sample and a prediction of risk can be made, in accordance with the methods of the first, second, third and fourth aspects of the invention.

The term "expression level" is used broadly to include a genomic expression profile, e.g. an expression profile of miRNAs. The expression level of the one or more miRNA molecules in the patient's sample and/or the control sample can be determined using any convenient means for determining a level of a nucleic acid sequence, e.g. quantitative nucleic acid hybridization of miRNA, labelled miRNA, and/or nucleic acid amplification techniques which are routinely use in the art and which the skilled person will be familiar with.

Preferred techniques for determining the miRNA expression level include:
  Real-time PCR (RT-PCR)—this technique is suitable for large scale/multiple analysis and so useful for screening large populations;
  Microarray—2D array on a solid substrate;
  Next generation sequencing platforms (e.g. RNAseq)— the advantages of next generation sequencing are that it is high throughput, fast and has a low cost per base; and
  In situ hybridisation.

The present inventors have identified the miRNAs listed in Table 1 and Table 2 as being useful in the context of the present invention. In preferred embodiments of each of the first, second, third or fourth aspects of the invention, the one or more miRNAs are selected from the group of miRNAs presented in Table 1. In particularly preferred embodiments the expression level of all nine of the miRNAs in Table 1 is determined.

TABLE 1

| miRNA | Nucleotide sequence | Accession No. | Direction of difference in expression compared to control |
|---|---|---|---|
| hsa-let-7a-5p | ugagguaguagguuguauaguu (SEQ ID NO. 1) | MIMAT0000062 | Increased |
| hsa-miR-374a-5p | uuauaauacaaccugauaagug (SEQ ID NO. 2) | MIMAT0000727 | Increased |
| hsa-miR-15b-5p | uagcagcacaucaugguuuaca (SEQ ID NO. 3) | MIMAT0000417 | Increased |
| hsa-miR-19b-3p | ugugcaaauccaugcaaaacuga (SEQ ID NO. 4) | MIMAT0000074 | Increased |
| hsa-miR-23a-3p | aucacauugccagggauuucc (SEQ ID NO. 5) | MIMAT0000078 | Increased |
| hsa-miR-93-5p | caaagugcuguucgugcagguag (SEQ ID NO. 6) | MIMAT0000093 | Increased |
| hsa-miR-150-5p | ucucccaacccuuguaccagug (SEQ ID NO. 7) | MIMAT0000451 | Increased |
| hsa-miR-185-5p | uggagagaaaggcaguuccuga (SEQ ID NO. 8) | MIMAT0000455 | Increased |
| hsa-miR-191-5p | caacggaaucccaaaagcagcug (SEQ ID NO. 9) | MIMAT0000440 | Increased |

TABLE 2

| miRNA | Nucleotide sequence | Accession No. | Direction of difference in expression compared to control |
|---|---|---|---|
| hsa-miR-106b-5p | uaaagugcugacagugcagau (SEQ ID NO. 10) | MIMAT0000680 | Increased |
| hsa-miR-22-3p | aagcugccaguugaagaacugu (SEQ ID NO. 11) | MIMAT0000077 | Increased |
| hsa-miR-26b-5p | uucaaguaauucaggauaggu (SEQ ID NO. 12) | MIMAT0000083 | Increased |
| hsa-let-7i-5p | ugagguaguaguuugugcuguu (SEQ ID NO. 13) | MIMAT0000415 | Increased |
| hsa-miR-4454 | ggauccgagucacggcacca (SEQ ID NO. 14) | MIMAT0018976 | Increased |
| hsa-miR-144-3p | uacaguauagaugauguacu (SEQ ID NO. 15) | MIMAT0000436 | Increased |
| hsa-miR-223-3p | ugucaguuugucaaauacccca (SEQ ID NO. 16) | MIMAT0000280 | Increased |
| hsa-miR-92a-3p | uauugcacuuguccggccugu (SEQ ID NO. 17) | MIMAT0000092 | Increased |
| hsa-let-7b-5p | ugagguaguagguugugugguu (SEQ ID NO. 18) | MIMAT0000063 | Increased |
| hsa-miR-188-5p | caucccuugcauggugagggg (SEQ ID NO. 19) | MIMAT0000457 | Decreased |
| hsa-miR-16-5p | uagcagcacguaaauauuggcg (SEQ ID NO. 20) | MIMAT0000069 | Increased |
| hsa-let-7g-5p | ugagguaguaguuuguacaguu (SEQ ID NO. 21) | MIMAT0000414 | Increased |
| hsa-miR-148b-3p | ucagugcaucacagaacuuugu (SEQ ID NO. 22) | MIMAT0000759 | Increased |
| hsa-miR-122-5p | uggagugugacaaugguguuug (SEQ ID NO. 23) | MIMAT0000421 | Increased |

Table 3 is a subset of the miRNAs listed in Table 2. In an embodiment of the first, second, third or fourth aspects of the invention, the one or more miRNAs may be selected from the group of miRNAs presented in Table 3.

TABLE 3

| miRNA | Nucleotide sequence | Accession No. | Direction of difference in expression compared to control |
|---|---|---|---|
| hsa-miR-106b-5p | uaaagugcugacagugcagau (SEQ ID NO. 10) | MIMAT0000680 | Increased |
| hsa-miR-22-3p | aagcugccaguugaagaacugu (SEQ ID NO. 11) | MIMAT0000077 | Increased |
| hsa-miR-26b-5p | uucaaguaauucaggauaggu (SEQ ID NO. 12) | MIMAT0000083 | Increased |
| hsa-let-7i-5p | ugagguaguaguuugugcuguu (SEQ ID NO. 13) | MIMAT0000415 | Increased |
| hsa-miR-4454 | ggauccgagucacggcacca (SEQ ID NO. 14) | MIMAT0018976 | Increased |
| hsa-miR-144-3p | uacaguauagaugauguacu (SEQ ID NO. 15) | MIMAT0000436 | Increased |

TABLE 3-continued

| miRNA | Nucleotide sequence | Accession No. | Direction of difference in expression compared to control |
|---|---|---|---|
| hsa-miR-223-3p | ugucaguuugucaaauacccca (SEQ ID NO. 16) | MIMAT0000280 | Increased |
| hsa-let-7b-5p | ugagguaguagguugugguu (SEQ ID NO. 18) | MIMAT0000063 | Increased |
| hsa-miR-188-5p | caucccuugcauggggaggg (SEQ ID NO. 19) | MIMAT0000457 | Decreased |
| hsa-miR-16-5p | uagcagcacguaaauauuggcg (SEQ ID NO. 20) | MIMAT0000069 | Increased |
| hsa-miR-148b-3p | ucagugcaucacagaacuuugu (SEQ ID NO. 22) | MIMAT0000759 | Increased |
| hsa-miR-122-5p | Uggagugugacaaugguguuug (SEQ ID NO. 23) | MIMAT0000421 | Increased |

For the avoidance of doubt, "hsa-" refers to *Homo sapiens* and is a standard abbreviation to differentiate the miRNAs from those of other species. The suffixes "3p" and "5p" denote 3 prime or 5 prime, respectively. These suffixes are used to distinguish two miRNAs originating from opposite arms of the same pre-miRNA. "let-7" refers to the lethal-7 gene, which is a miRNA precursor.

All miRNAs are identified herein using standard nomenclature. Sequence information for each of the miRNAs listed in Tables 1 and 2 can be found on the miRBase database maintained by Manchester University (www.mirbase.org).

The data shown in FIGS. 1-9 demonstrate the ability of each of the nine individual miRNAs listed in Table 1 to predict cervical shortening. The data shown in FIGS. 10-19 demonstrate the utility of the same nine miRNAs listed in Table 1 in predicting preterm birth.

Figure 20:
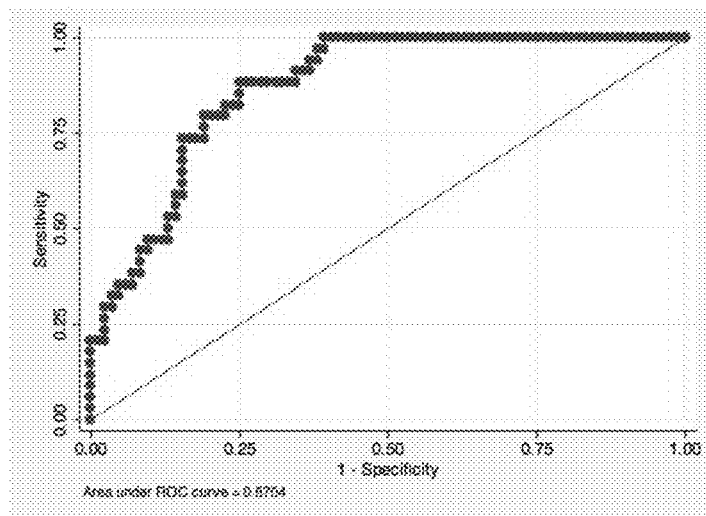
FIG. 20 shows a receiver operator characteristic curve describing the combined ability of plasma hsa-miR-150-5p, hsa-miR-19b-3p, hsa-miR-185-5p and hsa-miR-374a-5p to predict cervical shortening at 12-14$^{+6}$ weeks gestation (AUC=0.87).
Figure 21:
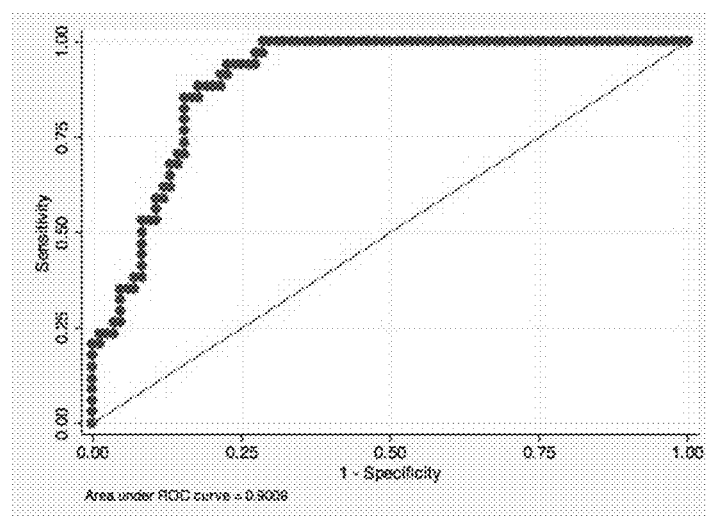
FIG. 21 shows a receiver operator characteristic curve describing the combined ability of all nine plasma microRNAs to predict cervical shortening at 12-14$^{+6}$ weeks gestation (AUC=0.90).

These data are supported by a further study carried out by the inventors, wherein the expression level of the nine specific miRNAs of Table 1 was determined in plasma from a second population of pregnant women at 12-14$^{+6}$ weeks gestation (n=87). The data generated in this follow-up study, shown in Table 4 below, and in FIGS. 19-21, replicate the initial findings of increased cell-free specific miRNA expression in plasma from women who exhibited subsequent cervical shortening. Table 4 shows the expression of specific plasma miRNAs at 12-14$^{+6}$ weeks gestation in women who went on to have cervical shortening (n=18) compared with women with no cervical shortening (n=69). Significantly higher expression of all nine microRNAs is observed in plasma from women who went on to have cervical shortening (cervical length <25 mm) compared with women with a normal cervical length.

TABLE 4

| MicroRNA | Mean fold change in expression | Inter-quartile range | P value | Area under receiver operator characteristic curve* |
|---|---|---|---|---|
| hsa-miR-93-5p | 3.1 | 0.8-3.9 | 0.0001 | 0.76 |
| hsa-miR-191-5p | 3.7 | 1.6-4.7 | 0.0001 | 0.79 |
| hsa-let-7a-5p | 2.2 | 0.9-2.4 | 0.0054 | 0.72 |
| hsa-miR-374a-5p | 4.2 | 1.5-5.1 | <0.0001 | 0.82 |
| hsa-miR-150-5p | 5.8 | 2.7-7.6 | <0.0001 | 0.86 |
| hsa-miR-15b-5p | 3.7 | 1.3-3.9 | <0.0001 | 0.79 |
| hsa-miR-185-5p | 3.6 | 1.1-4.2 | <0.0001 | 0.80 |
| hsa-miR-19b-3p | 3.1 | 0.8-3.9 | <0.0001 | 0.82 |
| hsa-miR-23a-3p | 5.1 | 1.5-6.7 | <0.0001 | 0.66 |

*Receiver operator characteristic curves were calculated using data from the original discovery population combined with the second validation cohort (n = 119).

The replication of the earlier findings in an independent population of women supports the inventors' hypothesis that specific miRNAs may act as peripherally available biomarkers of future cervical shortening and subsequent preterm birth. The inventors found that the combination of data from all nine microRNAs resulted in the strongest predictive power (see FIG. 21).

Since the miRNA markers listed in Table 1 and Table 2 are useful for predicting cervical shortening, they can also be used to predict the timing of the onset of labour at term, which is associated with cervical shortening. Therefore, the miRNA markers listed in Table 1 and Table 2 have utility for women who have reached at term, as well at preterm stages of pregnancy.

Therefore, a fourth aspect of the invention provides a method for predicting the timing of the onset of labour in a pregnant subject who is at term (>37 weeks gestation), comprising determining the expression level of one or more miRNA molecules identified in Table 1 or Table 2 extracted from a biological sample obtained from said subject and comparing to a control value, wherein a difference in the expression level of the one or more of the miRNA molecules compared to the control value indicates the timing of the onset of labour.

If the miRNA molecule that is detected using the method according to this aspect of the invention is a molecule whose over-expression is associated with cervical shortening, then an expression level of said miRNA in the patient's sample that is greater than the control value is indicative of onset of labour in said patient.

In a preferred embodiment of this aspect of the invention, the expression level of a combination of two or more of the miRNA molecules identified in Table 1, Table 2 or Table 3, and preferably a combination of three or four of the miRNA molecules identified in Table 1, Table 2 or Table 3 is determined. In this embodiment, the combined expression level of the two, three or four or more miRNA molecules is compared to the control value.

In a preferred embodiment, the expression level of a combination of all nine of the miRNAs identified in Table 1 is determined.

As used herein in relation to the fourth aspect of the invention, the term "control value" refers to the expression level of the corresponding miRNA molecule(s) in a corresponding control sample obtained from a cohort of pregnant female subjects who fail to go into labour spontaneously at 42 weeks gestation.

If the expression level of two or more miRNA molecules is determined in the method of the invention, the corresponding control value is the combined baseline expression level of the corresponding miRNAs in a control sample.

Preferably, as described above, the cut-off value for determining whether the expression level of a given miRNA molecule is "different" (elevated or reduced) compared with a control value is 3-times the baseline expression level for the miRNA.

In other aspects of the invention, the miRNA molecules identified in Tables 1 and/or 2 and/or 3 can be used to determine the likely response of a patient to agents used for induction of labour at any gestational age. Such agents include, for example, prostaglandins and oxytocin.

Furthermore, the miRNA molecules identified in Tables 1 and/or 2 and/or 3 can also be used to determine the risk of caesarean section associated with induction of labour, in a patient at any gestational age.

The present inventors have identified that differences in expression levels of miRNAs compared to a control value, which can predict preterm cervical shortening, are also predictive of easy induction of labour at term. Females who are going to go overdue (i.e. delivery at >40 weeks gestation) will have a longer cervix (and the associated levels of miRNA markers disclosed herein) and are likely to have a higher risk of induction failure and a higher risk of need for Caesarean section.

The fifth aspect of the invention provides a support material, which is a solid substrate, such as a biochip, comprising one or more probes specific for one or more of the miRNA molecules in Table 1 or Table 2 attached thereto or immobilised thereon. In a preferred embodiment, the support material comprises probes specific for each of the nine miRNA molecules identified in Table 1.

As used herein, the term "probe" refers to an oligonucleotide capable of binding to a target nucleic acid (i.e. a miRNA molecule) of complimentary sequence. Probes may bind to targets lacking complete complementarity with the probe sequence, depending upon the stringency of the hybridisation conditions. Probes may be directly labelled or indirectly labelled, such as with biotin to which a streptavidin complex may later bind.

The probes may be capable of hybridising to a target miRNA sequence under stringent hybridisation conditions. The probes may be attached at spatially defined locations on the substrate. The solid substrate may be a material that may be modified to contain discrete individual sites appropriate for the attachment or association of the probes and is amenable to at least one detection method. Examples of suitable substrates include glass and modified or functionalised glass, plastics, polysaccharides, nylon or nitrocellulose, resins, silica or silica-based materials, carbon and metals. The substrate may allow optical detection without appreciably fluorescing.

The substrate may be planar, although other configurations of substrates may be used as well. For example, probes may be positioned on the inside surface of a tube.

The support material and the probe may be derivatized with a chemical functional group, such that the probe may be attached using the functional group directly or indirectly using a linker. Alternatively, the probe may be attached to the solid support non-covalently, for example using biotinylated oligonucleotides. Alternatively the probe may be synthesised on the surface of the solid support using techniques such as photopolymerization and photolithography.

Preferably, the support material comprises oligonucleotide sequences specific to each of the one or more miRNA molecules. The support material can be used in a method according to any of the first, second, third or fourth aspects of the invention.

The present invention also provides kits for predicting risk of cervical shortening and/or preterm labour (PTL) in a pregnant female subject, comprising one or more probes specific for one or more of the miRNA molecules in Table 1 or Table 2. In addition, the kit may comprise any or all of the following: assay reagents, buffers, probes and/or primers, sterile saline or another pharmaceutically-acceptable emulsion and suspension base. In addition, kits may include instructions for use for the practice of the methods described herein.

A kit according to the invention may be used to carry out any of the methods described herein.

The invention will be further described with reference to the following non-limiting example.

EXAMPLE

Materials and Methods

Sample Collection and Study Design:

Following ethical approval, whole blood samples were collected from pregnant women attending the dedicated prematurity surveillance clinics at St. Mary's and Queen Charlotte's and Chelsea Hospitals, London. Blood was taken at three different time-points during pregnancy; 12+0-14+6 (time point A), 15+0-17+6 (time point B) and 19+0-21+6 (time point C), and stored. Approximately 3 ml of whole blood was obtained. The samples were placed on ice immediately and centrifuged at 1300 g for 10 minutes at 4° C. within 30 min of collection. Isolated plasma was stored in 1000 µl aliquots in natural RNAase free microtubes at −80° C. Samples demonstrating macroscopic haemolysis were discarded. Following delivery, samples were allocated to phenotypic cohorts depending on whether women went on to exhibit either cervical shortening and preterm delivery (n=25), cervical shortening and term delivery (n=31) or no cervical shortening with term delivery (n=48). (Preterm delivery not preceded by cervical shortening is very rare in this population).

RNA Extraction:

Plasma aliquots were thawed on ice. In order to minimise cellular and platelet contamination, samples were further spun at 800 g for 10 min at 4° C. The upper 750 ul was removed for onward processing and the remaining plasma discarded. RNA was extracted using the 'Plasma/Serum Circulating and Exosomal RNA Purification Mini Kit (Slurry Format)' (Norgen Biotek, Ontario, Canada) according to the manufacturer's instructions. In addition, 5000 attomoles synthetic cel-254 (sequence UGCAAAUC-UUUCGCGACUGUAGG (SEQ ID NO. 24), Integrated DNA Technologies BVBA, Leuven, Belgium) was spiked-in to the plasma following the addition of lysis and denaturing buffers to allow downstream normalisation of any technical variation to the extraction process. Eluted RNA was further purified and concentrated using Amicon Ultra YM-3 columns (Merck Millipore, Darmstadt, Germany).

nCounter™ Profiling:

RNA was sent externally for profiling using the nCounter™ plasma miRNA cassette (Nanostring, Seattle, USA). This technique permits target miRNA expression levels to be directly assessed, without enzymatic reactions, via two sequence-specific probes[11]. The individual mRNA is captured with one miRNA target sequence-specific capture probe that is then used in a post-hybridization affinity purification procedure. The second miRNA target specific-sequence and fluorescent-tagged, coded probe is then used in the detection with the 3-component complex separated on a surface via an applied electric field followed by microscopy imaging.

Reverse transcription and real time polymerase chain reaction: RNA was reverse transcribed to cDNA following the addition of 0.625 µl synthetic miRNA UniSp6 ($10^8$ copies/µl) (Exiqon, Vedbaek, Denmark) to allow downstream normalisation of any technical variation to the reaction. Real time polymerase chain reaction was performed using custom 'pick and mix' panels containing LNA™ primers, according to the manufacturer's instructions (Exiqon, Vedbaek, Denmark).

Data Analysis nCounter™

Background signal was defined as two standard deviations above the mean of negative control probes and subtracted from the raw miRNA molecule counts. Expression counts were normalised to the mean expression of the top 100 expressed miRNAs. MiRNA probes without expression above background in more than half of the samples from any clinical group were removed from further analysis. Samples with very high expression of platelet derived miRNAs hsa-miR-16 and hsa-miR-25 and hsa-miR-93 were removed from the analysis (n=2). Expression was compared between clinical groups using nSolver v2.0 software (Nanostring, Seattle, USA) and those miRNAs found to be differentially expressed with a false discovery rate <0.05 were considered to be discriminatory.

RT-PCR

Cycle threshold (Ct) values for each miRNA were calculated using stepone v2.3 software (Life Technologies Ltd, Paisley, UK). Ct values were median normalised firstly to an inter-plate calibrator and then to the extraction and reverse transcription spiked-in controls. Distributions were assessed for normality using the D'Agostino and Pearson omnibus test and clinical groups were compared using either Student's unpaired t or Mann-Whitney test as appropriate; a p value <0.05 was considered significant. Fold change was calculated using $2^{-DG}$ where DG=mean Ct experimental group−mean Ct normal group.

REFERENCES

1. Wood, N. S., Marlow, N., Costeloe, K., Gibson, A. T. & Wilkinson, A. R. Neurologic and developmental disability after extremely preterm birth. EPICure Study Group. *The New England journal of medicine* 343, 378-384 (2000).
2. Holst, R. M., et al. Prediction of spontaneous preterm delivery in women with preterm labor: analysis of multiple proteins in amniotic and cervical fluids. *Obstetrics and gynecology* 114, 268-277 (2009).
3. Mitchell, P. S., et al. Circulating microRNAs as stable blood-based markers for cancer detection. *Proceedings of the National Academy of Sciences of the United States of America* 105, 10513-10518 (2008).
4. Harper, K. A. & Tyson-Capper, A. J. Complexity of COX-2 gene regulation. *Biochemical Society transactions* 36, 543-545 (2008).
5. Luense, L. J., Carletti, M. Z. & Christenson, L. K. Role of Dicer in female fertility. *Trends in endocrinology and metabolism: TEM* 20, 265-272 (2009).
6. Morita, S., et al. One Argonaute family member, Eif2c2 (Ago2), is essential for development and appears not to be involved in DNA methylation. *Genomics* 89, 687-696 (2007).
7. Mouillet, J. F., et al. The levels of hypoxia-regulated microRNAs in plasma of pregnant women with fetal growth restriction. *Placenta* 31, 781-784 (2010).
8. Renthal, N. E., et al. miR-200 family and targets, ZEB1 and ZEB2, modulate uterine quiescence and contractility during pregnancy and labor. *Proceedings of the National Academy of Sciences of the United States of America* 107, 20828-20833 (2010).
9. Williams, K. C., Renthal, N. E., Condon, J. C., Gerard, R. D. & Mendelson, C. R. MicroRNA-200a serves a key role in the decline of progesterone receptor function leading to term and preterm labor. *Proceedings of the National Academy of Sciences of the United States of America* 109, 7529-7534 (2012).
10. Hassan, S. S., et al. MicroRNA expression profiling of the human uterine cervix after term labor and delivery. *American journal of obstetrics and gynecology* 202, 80 e81-88 (2010).
11. Geiss, G. K., et al. Direct multiplexed measurement of gene expression with color-coded probe pairs. *Nature biotechnology* 26, 317-325 (2008).
12. Campbell, S. Universal cervical-length screening and vaginal progesterone prevents early preterm births, reduces neonatal morbidity and is cost saving: doing nothing is no longer an option. *Ultrasound in obstetrics & gynecology the official journal of the International Society of Ultrasound in Obstetrics and Gynecology* 38, 1-9 (2011).
13. Romero, R., et al. A blueprint for the prevention of preterm birth: vaginal progesterone in women with a short cervix. *Journal of perinatal medicine* 41, 27-44 (2013).
14. Montenegro, D., et al. Differential expression of microRNAs with progression of gestation and inflammation in the human chorioamniotic membranes. *Am. J Obstet Gynecol.* 2007 September; 197(3): 289.e1-289.e6.

The invention claimed is:

1. A method for reducing a risk of cervical shortening or preterm labor (PTL) comprising:
   determining an elevated expression level of an miRNA molecule having SEQ ID NO: 2 extracted from a biological sample obtained from a pregnant subject as compared to a control value; and
   administering to the pregnant subject one or more of cervical ultrasound screening, therapeutic intervention, and/or surgical intervention.

2. The method according to claim 1, wherein the therapeutic intervention is selected from one or more of oxytocin receptor antagonists, prostaglandin receptor antagonists, beta-adrenergic receptor agonists, nitrogen oxide donors, magnesium sulfate, prostaglandin-synthase inhibitors, non-steroidal anti-inflammatory drugs (NSAIDs), small molecule and other anti-inflammatory drugs, calcium channel blockers, progesterone, 17-a-hydroxyprogesterone caproate, and progesterone analogues.

3. The method according to claim 1, wherein the biological sample is a whole blood sample.

4. The method according to claim 3, wherein the miRNA molecule is extracted from either serum or plasma component of the whole blood sample.

5. The method according to claim 1, wherein the expression level of a combination of SEQ ID NO:2 and one or more miRNA molecules selected from SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23 is determined, and wherein the combined expression level of the miRNA molecules is compared to the control value.

6. The method according to claim 5, wherein the expression level of a combination of SEQ ID NO:2 and two, three or four miRNA molecules selected from SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23 is determined, and wherein the combined expression level of SEQ ID NO:2 and the two, three or four miRNA molecules is compared to the control value.

7. The method according to claim 1, wherein the method is carried out at between 12 to 24 weeks gestation.

8. The method according to claim 7, wherein the method is carried out at between 12 to 16 weeks gestation, and/or at between 16 to 18 weeks gestation, and/or at between 18 to 24 weeks gestation.

9. A method for inducing labor in a pregnant subject who is at or more than 37 weeks gestation, comprising:
   determining an elevated expression level of a miRNA molecule having SEQ ID NO:2 extracted from a biological sample obtained from the pregnant subject compared to a control value; and
   administering to the pregnant subject an agent used for induction of labor.

10. The method according to claim 1, wherein the expression levels of nine miRNA molecules having SEQ ID NOs:1-9 are determined, and wherein the combined expression level of the nine miRNA molecules is compared to the control value.

11. The method according to claim 9, wherein the control value is the expression level of the corresponding miRNA molecule(s) in a corresponding control sample obtained from a cohort of pregnant female subjects who fail to go into labor spontaneously by 42 weeks gestation.

12. The method according to claim 1, wherein the expression level of the miRNA molecule is determined using one or more testing methods selected from the group consisting of nucleic acid hybridization, nucleic acid amplification, real-time PCR, microarray, Next generation sequencing platforms, and in situ hybridization.

13. The method of claim 9, wherein the expression levels of nine miRNA molecules having SEQ ID NOs:1-9 are determined, and wherein the combined expression level of the nine miRNA molecules is compared to the control value.

14. The method according to claim 9, wherein the biological sample is a whole blood sample.

15. The method according to claim 14, wherein the miRNA molecule is extracted from either the serum or plasma component of the whole blood sample.

* * * * *